United States Patent
Hoelscher

(10) Patent No.: US 7,615,526 B2
(45) Date of Patent: Nov. 10, 2009

(54) FURANOID AND PYRANOID C14-C18-OXABICYCLOALKANONES AS ODORIFEROUS AND/OR AROMA SUBSTANCES

(75) Inventor: Bernd Hoelscher, Halle (DE)

(73) Assignee: SYMRISE GmbH & Co. KG, Holzminden (DE)

( * ) Notice: Subject to any disclaimer, the term of this patent is extended or adjusted under 35 U.S.C. 154(b) by 0 days.

(21) Appl. No.: 12/051,873

(22) Filed: Mar. 20, 2008

(65) Prior Publication Data

US 2008/0234174 A1    Sep. 25, 2008

(30) Foreign Application Priority Data

Mar. 21, 2007  (EP) .................................. 07104595
Oct. 2, 2007  (EP) .................................. 07117747

(51) Int. Cl.
  *A61Q 13/00*  (2006.01)
  *C07C 49/00*  (2006.01)
  *C07C 205/00*  (2006.01)

(52) U.S. Cl. .................. 512/17; 568/325; 568/585; 512/23

(58) Field of Classification Search ............ 512/8, 512/23, 17; 252/522 R; 568/325, 585
See application file for complete search history.

(56) References Cited

U.S. PATENT DOCUMENTS

| 3,816,534 A | | 6/1974 | Lemberg et al. |
| 4,541,950 A | * | 9/1985 | Van Loveren et al. .......... 512/8 |
| 6,326,349 B1 | | 12/2001 | Helmlinger et al. |

FOREIGN PATENT DOCUMENTS

| EP | 0103893 A2 | 3/1984 |
| EP | 0983989 A1 | 3/2000 |
| EP | 1099699 A1 | 5/2001 |

OTHER PUBLICATIONS

Shapiro R. H. "Alkenes from Tosylhydrazones" Organic Reactions 23 p. 501. 1976, Chapter 3, Table IV, Item line 15.*
Schreiber et al. Item XX, p. 2105 of table in Helvetica Chimica Acta 1967 vol. 50 No. 220 pp. 2101-2108.*
R.H. Shapiro, "Alkenes from Tosylhydrazones" in Organic Reactions vol. 23 p. 501 1976 Chapter 3 Table IV item line 15.*
Tochtermann, et al., "Diastereoselektive synthese eines punktionalisierten 2,5-uberbruckten tetrahydrofurans", Tetrahydron. 1988, vol, 44, No. 15, pp. 4797-4804.
Kraft, et al., "Constructing conformationally constrained macrobicyclic musks", Chem. Eur. J., 2001, vol. 7, No. 15, pp. 3254-3262.
Behr, et al. "Synthesis of γ-Lactones from Cycloocta-1,5-diene—Starting Materials for Natural-Product Synthesis," *Eur. J. Org. Chem.*, 2004, pp. 3884-3892.
Williams, Alvin S., "The Synthesis of Macrocyclic Musks," *Synthesis*, 1999, No. 10, pp. 1707-1723.
Ohloff, Günther. *Scent and Fragrances: The Fascination of Odors and their Chemical Perspectives*, Springer-Verlag, pp. 204-211.

* cited by examiner

*Primary Examiner*—James Seidleck
*Assistant Examiner*—Aaron Greso
(74) *Attorney, Agent, or Firm*—Connolly Bove Lodge & Hutz LLP

(57) ABSTRACT

The present invention relates to compounds of the formula (I) and the formula (Ia)

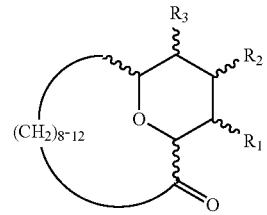

Formula (I)

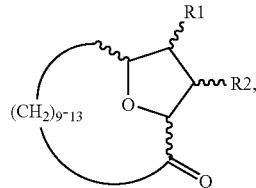

Formula (Ia)

wherein $R_1$, $R_2$ and $R_3$ mutually independently mean hydrogen or methyl, odoriferous and/or aroma substance compositions comprising one or more compounds according to the invention of the formula (I) and/or formula (Ia), perfumed products and aromatized products in each case comprising one or more compounds according to the invention of the formula (I) and/or formula (Ia), and to uses of one or more compounds according to the invention of the formula (I) and/or formula (Ia) as odoriferous and/or aroma substances and methods of producing compounds according to the invention of the formula (I) and formula (Ia).

20 Claims, No Drawings

FURANOID AND PYRANOID C14-C18-OXABICYCLOALKANONES AS ODORIFEROUS AND/OR AROMA SUBSTANCES

This application claims benefit of European application 07104595.9 filed Mar. 21, 2007 and European application 07117747.1 filed Oct. 2, 2007.

The present invention relates to compounds of the formula (I) and the formula (Ia)

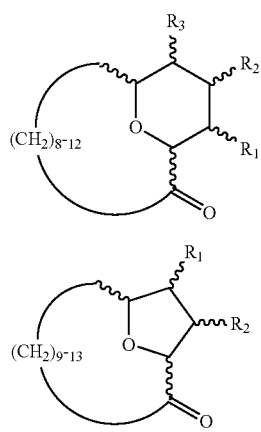

Formula (I)

Formula (Ia)

wherein $R_1$, $R_2$ and $R_3$ mutually independently mean hydrogen or methyl, odoriferous and/or aroma substance compositions comprising one or more compounds according to the invention of the formula (I) and/or formula (Ia), to perfumed products and aromatized products in each case comprising one or more compounds according to the invention of the formula (I) and/or formula (Ia), and to uses of one or more compounds according to the invention of the formula (I) and/or formula (Ia) as odoriferous and/or aroma substances and to methods of producing compounds according to the invention of the formula (I) and formula (Ia).

Despite a plurality of odoriferous and/or aroma substances already in existence, there still remains a general need within the perfume industry for novel odoriferous and/or aroma substances. For instance, there is a need for odoriferous and/or aroma substances with interesting fragrance notes of the musk type, which are capable of producing, in addition to a musk-like fragrance note, further interesting odor notes in odoriferous and/or aroma substance compositions and, with their novel or original fragrance properties, of broadening the options open to the perfumer. In particular, there is interest in odoriferous and/or aroma substances with musk-like fragrance notes which are capable of entering into a harmonious combination with flowery-smelling odoriferous substances The odorous aspects and notes should preferably combine in order, in so doing, to provide an overall complex odor impression.

For the purpose of creating novel modern compositions, there is a constant need for odoriferous substances with particular odorous properties which are suitable for acting as the basis for the composition of novel modern perfumes with complex odor properties. Odoriferous substances which preferably sought should, in addition to a musk-like fragrance note, comprise further notes and aspects which impart odorous character and complexity thereto.

The search for suitable odoriferous and/or aroma substances, which led to the present invention, was complicated by the following factors:

The mechanisms of odor perception are not sufficiently known.

The interrelationships between specific odor perception, on the one hand, and the chemical structure of the associated odoriferous substance, on the other hand, have not been adequately investigated.

Even slight modifications to the structure of a known odoriferous substance often bring about major changes to organoleptic properties and impair compatibility with the human body.

The success of the search for suitable odoriferous substances is thus highly dependent on the searcher's intuition.

The object underlying the present invention thus primarily involved identifying musk-like odoriferous and/or aroma substances, in particular those which are combined with further interesting and original properties as regards odor and/or flavor, whereby the sought odoriferous and/or aroma substances permit novel and original odoriferous and/or aroma substance compositions with particular odorous notes and aspects. In particular, odoriferous and/or aroma substances with musk-like notes were to be identified which are in particular suitable for combination with odoriferous and/or aroma substances which exhibit a woody, flowery or woody-flowery fragrance note.

In addition, the odoriferous and/or aroma substances fulfilling this main object should furthermore preferably have one or more additional positive secondary properties extending beyond their primary properties, namely regarding odor and/or flavor, such as for example greater stability under specific conditions of use, a low threshold value, higher yield, improved tenacity, elevated intrinsic substantivity together with an improvement in the substantivity of further odoriferous and/or aroma substances, a notable booster action or strong blooming, such that notable organoleptic effects or alternatively also better dermatological and toxicological properties may be achieved relative to comparable odoriferous and/or aroma substances.

The present primary object is achieved by providing the compounds of the formula (I) and formula (Ia)

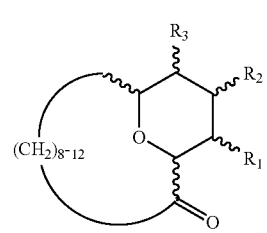

Formula (I)

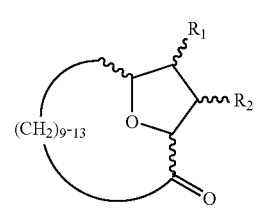

Formula (Ia)

wherein $R_1$, $R_2$ and $R_3$ mutually independently mean hydrogen or methyl.

The present invention secondly provides an odoriferous and/or aroma substance composition (perfume composition) comprising or consisting of
a) one, two, three, four or more compounds according to the invention of the formula (I) and/or formula (Ia)

and
B) one, two, three or more further odoriferous and/or aroma substances, which are not compounds of the formula (I) and formula (Ia), as described above.

The present invention thirdly provides a perfumed cosmetics or domestic product comprising or consisting of
a) one, two, three, four or more compounds according to the invention of the formula (I) and/or formula (Ia) and/or
b) one, two, three or more odoriferous and/or aroma substance compositions according to the invention and
c) one or more further basic substances, auxiliary substances and/or additives.

The present invention fourthly provides aromatized products, which serve for nutrition, oral care and/or pleasure, and semifinished products for this purpose or seasoning mixtures comprising or consisting of
a) one, two, three, four or more compounds according to the invention of the formula (I) and/or formula (Ia) as described above and/or
b) one, two, three or more odoriferous and/or aroma substance compositions according to the invention and
c) one or more further basic substances, auxiliary substances and/or additives.

The present invention fifthly provides the use of one, two, three, four or more compounds according to the invention of the formula (I) and/or formula (Ia) as odoriferous and/or aroma substances.

The present invention sixthly provides a method of imparting, modifying and/or enhancing an odor or flavor with one, a plurality of or all the musk-like notes,
wherein an organoleptically effective quantity of one, two, three, four or more compounds according to the invention of the formula (I) and/or formula (Ia)
or
an organoleptically effective quantity of one or more odoriferous or aroma substance compositions according to the invention comprising one, two, three, four or more compounds according to the invention of the formula (I) and/or formula (Ia) is brought into contact or mixed with a product.

The present invention seventhly provides a method of producing one or more compounds of the formula (I)

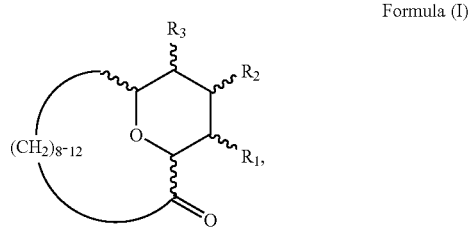

Formula (I)

wherein $R_1$, $R_2$ and $R_3$ mutually independently mean hydrogen or methyl, comprising or consisting of the following steps:

a) epoxidation of a compound of the formula (II) to yield a corresponding compound of the formula (III)

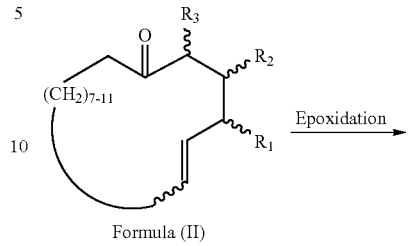

Formula (II)

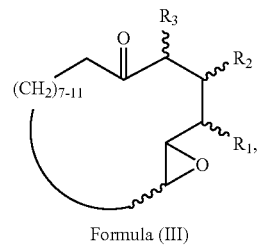

Formula (III)

wherein $R_1$, $R_2$ and $R_3$ have the above-stated meanings,
b) subsequent reduction of the corresponding compound of the formula (III) to yield a corresponding compound of the formula (IV)

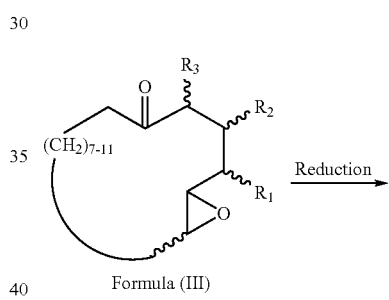

Formula (III)

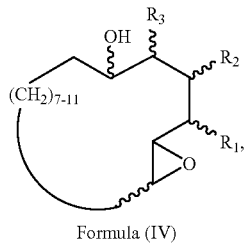

Formula (IV)

wherein $R_1$, $R_2$ and $R_3$ have the above-stated meanings,
c) subsequent cyclization of the corresponding compound of the formula (IV) to yield a corresponding compound of the formula (V)

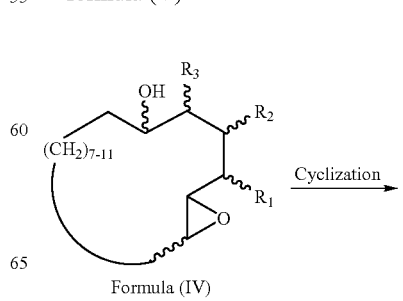

Formula (IV)

-continued

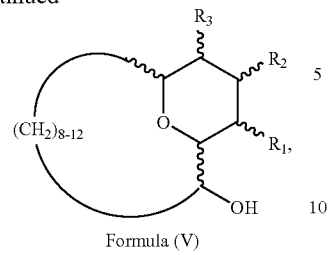

Formula (V)

wherein $R_1$, $R_2$ and $R_3$ have the above-stated meanings and d) subsequent oxidation of the corresponding compound of the formula (V) to yield a corresponding compound of the formula (I)

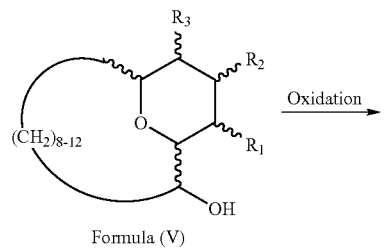

wherein $R_1$, $R_2$ and $R_3$ have the above-stated meanings.

The present invention eighthly provides a method of producing one or more compounds of the formula (Ia)

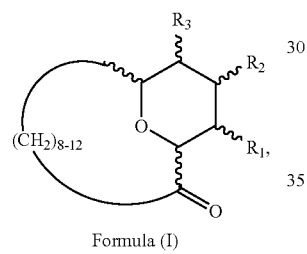

Formula (Ia)

wherein, $R_1$ and $R_2$ mutually independently mean hydrogen or methyl, comprising or consisting of the following steps:

a) reduction of a compound of the formula (IIa) to yield a corresponding compound of the formula (IIIa)

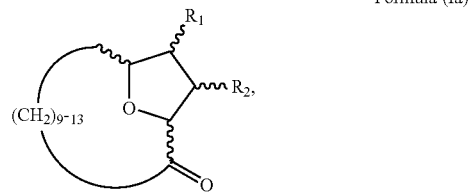

-continued

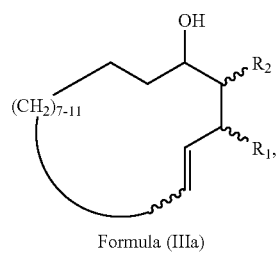

Formula (IIIa)

wherein $R_1$ and $R_2$ have the above-stated meanings, b) subsequent epoxidation of the corresponding compound of the formula (IIIa) to yield a corresponding compound of the formula (IVa)

wherein $R_1$ and $R_2$ have the above-stated meanings, c) subsequent cyclization of the corresponding compound of the formula (IVa) to yield a corresponding compound of the formula (Va)

wherein $R_1$ and $R_2$ have the above-stated meanings and
d) subsequent oxidation of the corresponding compound of the formula (Va) to yield a corresponding compound of the formula (Ia)

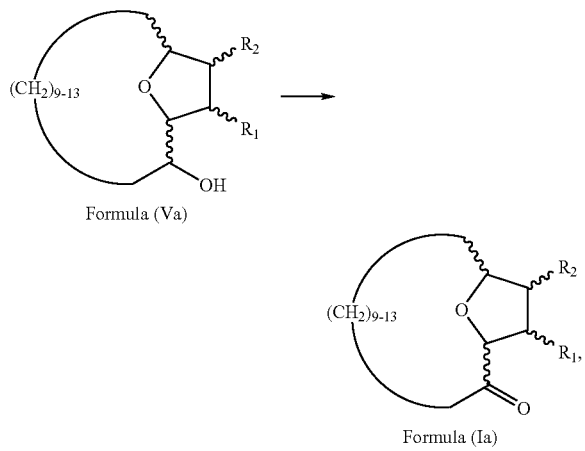

Formula (Va)

Formula (Ia)

wherein $R_1$ and $R_2$ have the above-stated meanings.

Further aspects, in particular preferred aspects the present invention are reproduced in the attached claims and the following detailed description.

According to the prior art, the field of odoriferous and aroma substance chemistry is deemed to have been thoroughly investigated. It is therefore particularly surprising that it has now proven possible to identify novel, valuable odoriferous and/or aroma substances in the area of musk odoriferous substances. The compounds according to the invention of the formula (I) and formula (Ia) have wholly independent olfactory properties, which stand out clearly from the known odoriferous substances and indeed are superior thereto. The suitability of the compounds of the formula (I) and formula (Ia) to be used according to the invention as odoriferous and/or aroma substances for use in the odor and aroma industry was hitherto unknown and is surprising.

According to the present invention, the term "compounds of the formula (I) and formula (Ia)" means that, where two, three, four or more compounds are used, is these are selected both from the group of the formula (I) and the group of the formula (Ia).

Preferably, the ratio of the total quantity of compounds of the formula (I) in a blend according to the invention to the total quantity of compounds of the formula (Ia) ranges from 100:1 to 1:10, preferably from 3:1 to 1:3, particularly preferably from 2:1 to 1:1.

According to the present invention, the term "compounds of the formula (I) or formula (Ia)" means that one, two, three, four or more compounds are selected solely from the group of the formula (I) or the group of the formula (Ia).

The compounds according to the invention of the formula (I) and formula (Ia) are optical isomers and may accordingly be E or Z configured. For the present invention, both pure isomers and mixtures thereof, in particular racemates, may be used. Odor properties may differ for the E and Z isomers.

For the present invention, E or Z isomers and the racemates thereof of the following compounds of the formula (I) are preferred:

wherein
$R_1$ means methyl and $R_2$ and $R_3$ mean hydrogen or
$R_1$ and $R_3$ mean hydrogen and $R_2$ means methyl or
$R_1$ and $R_2$ mean hydrogen and $R_3$ means methyl or
$R_1$, $R_2$ and $R_3$ mean hydrogen.

For the present invention, E or Z isomers and the racemates thereof of the following compounds of the formula (I) are particularly preferred:
14-oxa-bicyclo[8.3.1]tetradecan-2-one, 15-oxa-bicyclo[9.3.1]pentadecan-2-one, 16-oxa-bicyclo-[10.3.1]hexadecan-2-one, 17-oxa-bicyclo[11.3.1]heptadecan-2-one, 18-oxa-bicyclo[12.3.1]octadecan-2-one, 13-methyl-16-oxa-bicyclo[10.3.1]-hexadecan-2-one, 14-methyl-16-oxa-bicyclo[10.3.1]hexadecan-2-one and 15-methyl-16-oxa-bicyclo[10.3.1]hexadecan-2-one.

Very particularly preferred are:
17-oxa-bicyclo[11.3.1]heptadecan-2-one and 14-methyl-16-oxa-bicyclo[10.3.1]-hexadecan-2-one Of the isomers, the E isomers are particularly preferred.

Compounds according to the invention of the formula (I), in particular with preferred meanings for $R_1$, $R_2$ and $R_3$ the particularly and very particularly preferred compounds of the formula (I) and the preferred E isomers thereof may be used for all aspects of the present invention. Where the description of the invention, in particular below, but also above, refers to compounds (according to the invention) of the formula (I), these also include all the preferred developments thereof.

For the present invention, E or Z isomers and the racemates thereof of the following compounds of the formula (Ia) are preferred:

wherein
$R_1$ means methyl and $R_2$ means hydrogen or
$R_1$ means hydrogen and $R_2$ means methyl or
$R_1$ and $R_2$ mean hydrogen.

For the present invention, E or Z isomers and the racemates thereof of the following compounds of the formula (Ia) are particularly preferred:
14-oxa-bicyclo[9.2.1]tetradecan-2-one, 15-oxa-bicyclo[10.2.1]pentadecan-2-one, 16-oxa-bicyclo[11.2.1]hexadecan-2-one, 17-oxa-bicyclo[12.2.1]heptadecan-2-one, 18-oxa-bicyclo[13.2.1]octadecan-2-one, 13-methyl-16-oxa-bicyclo-[9.3.1]hexadecan-2-one, 14-methyl-16-oxa-bicyclo[11.2.1]hexadecan-2-one and 15-methyl-16-oxa-bicyclo[11.2.1]hexadecan-2-one.

Very particularly preferred are:
16-oxa-bicyclo[11.2.1]hexadecan-2-one and 15-methyl-16-oxa-bicyclo[11.2.1]-hexadecan-2-one Compounds according to the invention of the formula (Ia), in particular with preferred meanings for $R_1$ and $R_2$, the particularly and very particularly preferred compounds of the formula (I) and the preferred E isomers thereof may be used for all aspects of the present invention. Where the description of the invention, in particular below, but also above, refers to compounds (according to the invention) of the formula (Ia), these also include all the preferred developments thereof.

Since the compounds according to the invention of the formula (I) and formula (Ia) are novel, no organoleptic description thereof has hitherto been made. Our own investigations have revealed that compounds according to the invention of the formula (I) and formula (Ia) have musk-like odor properties.

The odor properties of 17-oxa-bicyclo[11.3.1]heptadecan-2-one are described as follows for the individual isomers:
Odor description, Z-isomer: weak musk odor, slightly leathery animal odor
Odor description, E-isomer: very strong clean musk odor, interesting delicate erogenous fragrance note, very natural odor impression.

The odor properties of 14-methyl-16-oxa-bicyclo[10.3.1]hexadecan-2-one are described as follows for the individual isomers:
Odor description, isomer 1: pleasant mellow musk-like odor
Odor description, isomer 2: pleasant mellow musk-like odor
Odor description, isomer 3: pleasant mellow musk-like odor
Odor description, isomer 4: pleasant mellow musk-like odor.

The odor properties of 16-oxa-bicyclo[11.2.1]hexadecan-2-one are described as follows for the individual isomers:
Odor description of the E/Z isomer: both have a very strong, clean musk odor with interesting delicate erogenous fragrance note, very natural odor impression.

The odor properties of 15-methyl-16-oxa-bicyclo[11.2.1]hexadecan-2-one are described as follows for the individual isomers:
Odor description, isomer 1: pleasant mellow musk-like odor
Odor description, isomer 2: pleasant mellow musk-like odor
Odor description, isomer 3: pleasant mellow musk-like odor
Odor description, isomer 4: pleasant mellow musk-like odor.

A structurally similar compound, namely 9-oxabicyclo[3.3.1]nonan-2-one, is known from Eur. J. Org. Chem. 2004, (18), 3884-3892. However, no organoleptic description of this compound was provided therein.

Further structurally similar compounds are known from the references (A. S. Williams, The Synthesis of Macrocyclic Musks; Synthesis 1999, 1707-1723; G. Ohloff, Riechstoffe und Geruchssinn [Odoriferous substances and the sense of smell], Springer Verlag). Odor descriptions from our own investigations and from the references may be summarized as follows:
1. 3,4,5,6,7,8,9,10,11,12,13,14-dodechydro-2H-1-oxa-benzocyclododecene: no musk-like odor, slightly woody
2. tetradecanhydro-1-oxa-benzocyclododecene: no musk-like odor, slightly woody Thus, these odor descriptions do not allow any conclusions to be drawn about the musk-like odor and/or flavor notes of the compounds according to the invention of the formula (I) and formula (Ia).

According to the second aspect of the present invention, one, two, three, four or more compounds according to the invention of the formula (I) and/or formula (Ia) are conventionally used in organoleptically effective quantities in odoriferous and/or aroma compositions, an odoriferous and/or aroma substance composition according to the invention preferably comprising a total quantity of one or more compounds according to the invention of the formula (I) and/or formula (Ia) in component (a) which is sufficient in this composition to impart, modify and/or enhance an odor and/or flavor with one, a plurality of or all of the musk-like notes.

A further preferred odoriferous and/or aroma substance composition is characterized in that the composition comprises a total quantity of one or more compounds according to the invention of the formula (I) and/or formula (Ia) in component (a) which is sufficient to impart to this composition a radiance, roundness and/or harmony and/or to enhance further odor and/or flavor notes of this composition.

A further preferred odoriferous and/or aroma substance composition according to the invention is characterized in that one, two, three or more odoriferous and/or aroma substances of the component (b) display a woody odor note and/or flavor note or one, two, three or more odoriferous and/or aroma substances of the component (b) display a flowery odor note and/or flavor note or one, two, three or more odoriferous and/or aroma substances of the component (b) display a woody and flowery odor note and/or flavor note.

According to the invention, odoriferous and/or aroma substance compositions which comprise or consist of one, two, three, four or more compounds according to the invention of the formula (I) and/or formula (Ia) may conventionally be used in liquid form, undiluted or diluted with a solvent, for perfuming or aromatization purposes.

Preferably, odoriferous and/or aroma substance compositions according to the invention additionally comprise one or more solvents. Solvents suitable for this purpose are preferably ethanol, isopropanol, diethylene glycol monoethyl ether, glycerol, propylene glycol, 1,2-butylene glycol, dipropylene glycol, diethyl phthalate, triethyl citrate, isopropyl myristate and triacetin.

A further preferred odoriferous and/or aroma substance composition according to the invention is characterized in that the composition is partially or completely adsorbed on a carrier.

As a result of this adsorption, a fine distribution of the odoriferous and/or aroma substances in the product and/or controlled release on use may preferably be established, Suitable carriers are preferably selected from the group consisting of porous inorganic materials, preferably such as sodium sulfate, silica gels, zeolites, gypsums, clays, clay granules, aerated concrete etc., or organic materials such as woods, cellulose-based substances, sugars, dextrins (for example maltodextrin), or plastics such as PVC, polyvinyl acetates or polyurethanes. The combination of odoriferous and/or aroma substance composition according to the invention and one or more carriers is one example of a perfumed or aromatized product according to the invention.

A further preferred odoriferous and/or aroma substance composition according to the invention is characterized in that the composition is partially or completely microencapsulated and/or spray-dried or present as inclusion complexes or as extrusion products.

Such products correspond either to a perfumed or aromatized product according to the invention or are added to the perfumed or aromatized product according to the invention preferably in this form.

Microencapsulation of the odoriferous and/or aroma substance compositions according to the invention to yield perfumed or aromatized products according to the invention may preferably be effected using the "coacervation" process with the assistance of capsule materials, for example of polyurethane-type substances or soft gelatins.

The spray-dried odoriferous and/or aroma substance compositions according to the invention may preferably be produced by spray drying an emulsion or dispersion containing the odoriferous and/or aroma substance composition, wherein modified starches, proteins, dextrin and vegetable gums may preferably be used as carriers.

Inclusion complexes may be produced for example by introducing dispersions of the odoriferous and/or aroma substance composition according to the invention together with cyclodextrins or urea derivatives into a suitable solvent, preferably water.

Extrusion products may be produced by melting odoriferous and/or aroma substance compositions according to the invention with a suitable waxy substance and extrusion with subsequent solidification, optionally in a suitable solvent, preferably isopropanol.

Such a modified, preferred odoriferous and/or aroma substance composition according to the invention is preferably coated with suitable materials for targeted odoriferous and/or aroma substance release.

By "coating" with suitable materials, the properties of the odoriferous and/or aroma substance compositions according to the invention are further optimized with regard to more targeted fragrance release, waxy plastics such as polyvinyl alcohol preferably being used. The resultant products in turn constitute perfumed or aromatized products according to the invention.

The further odoriferous and/or aroma substances according to component (b) of the odoriferous and/or aroma substance compositions according to the invention conventionally comprise other odoriferous and/or aroma substances. The ratio by weight of the total quantity of compounds to be used according to the invention of the formula (I) and/or formula (Ia) from component (a) to the total quantity of further odoriferous and/or aroma substances of component (b) preferably ranges from 1:1000 to 1:0.5.

In odoriferous and/or aroma substance compositions according to the invention, one, two, three, four or more compounds to be used according to the invention of the formula (I) and/or formula (Ia) are capable, when blended with one, two, three or more further odoriferous and/or aroma substances, of enhancing the intensity of the further odoriferous and/or aroma substances even at low rates of addition and/or of rounding and/or harmonizing the overall picture of the odoriferous substance blend and/or imparting greater radiance and naturalness to the blend.

By combining one, two, three, four or more compounds according to the invention of the formula (I) and/or formula (Ia) with one, two, three or more further odoriferous and/or aroma substances with preferably woody and/or flowery odor and/or flavor, novel odoriferous and/or aroma substance compositions may be formed. Particularly interesting and natural novel and original fragrance notes may be created in this manner. Preferred further (other) odoriferous and/or aroma substances of component (b) of the odoriferous and/or aroma substance composition according to the invention, which are preferably suitable for combination with one or more compounds according to the invention of the formula (I) and/or formula (Ia), may be found for example in S. Arctander, Perfume and Flavor Materials, Vols. I and i, Montclair, N.J. 1969, private publication, or K. Bauer et al., Common Fragrance and Flavor Materials, 4th Edition, Wiley-VCH, Weinheim 2001. Specifically, the following are mentioned as particularly preferred further odoriferous and/or aroma substances of component (b) of the odoriferous and/or aroma substance compositions according to the invention:

Extracts of natural raw materials, such as essential oils, concretes, absolutes, resins, resinoids, balsams, tinctures preferably selected from the group comprising ambergris tincture; amyris oil; angelica seed oil; angelica root oil; anise oil; valerian oil; basil oil; tree moss absolute; bay oil; artemisia oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassie absolute; castoreum absolute cedar leaf oil; cedarwood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; pine-needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil, blue; camomile oil, Roman; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil, distilled; lime oil, pressed; linaloe oil; Litsea cubeba oil; bay leaf oil; mace oil; marjoram oil; mandarin oil; massoia bark oil; mimosa absolute; ambrette oil; musk tincture; muscatel sage oil; nutmeg oil; myrrh absolute; myrrh oil; myrtle oil; clove leaf oil; clove bud oil; neroli oil; olibanum absolute; olibanum oil; opopanax oil; orange blossom absolute; orange oil; origanum oil; paimarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; sage oil, Dalmatian; sage oil, Spanish; sandalwood oil; celery seed oil; spike lavender oil; star anise oil; styrax oil; tagetes oil; fir needle oil; tea tree oil; terpentine oil; thyme oil; Tolu balsam; tonka absolute; tuberose absolute; vanilla extract; violet leaf absolute; verbena oil; vetiver oil; juniper berry oil; Cognac oil; wormwood oil; wintergreen oil; ylang ylang oil; hyssop oil; civet absolute; cinnamon leaf oil; cinnamon bark oil, and fractions thereof, or constituents isolated therefrom.

Individual odoriferous substances are preferably selected from the group consisting of hydrocarbons, such as preferably 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as preferably hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and the acetals thereof, such as preferably hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; 1-(1-methoxypropoxy)-(E/Z)-3-hexene;

aliphatic ketones and the oximes thereof, such as preferably 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds, such as preferably 3-methylthio-hexanol; 3-methylthiohexyl acetate; 3-mercaptohexanot; 3-mercaptohexyl acetate; 3-mercaptohexyl butyrate; 3-acetylthiohexyl acetate; 1-menthen-8-thiol;

aliphatic nitrites, such as preferably 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids, such as preferably (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

acyclic terpene alcohols, such as preferably citroneltol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

acyclic terpene aldehydes and ketones, such as preferably geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal;

cyclic terpene alcohols, such as preferably menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

cyclic terpene aldehydes and ketones, such as preferably menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedryl ketone);

cyclic alcohols, such as preferably 4-tert.-butylcyclohexanol; 3,3,5-trimethylcyclohexanol; 3-isocamphylcyclohexanol; 2,6,9-trimethyl-Z2,Z5, E9-cyclododecatrien-1-ol; 2-isobutyl-4-methyltetrahydro-2H-pyran-4-ol;

cycloaliphatic alcohols, such as preferably alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trmethylcyclohexyl)pentan-3-ol; 1-(2,2,6-trimethylcyclohexyl) hexan-3-ol;

cyclic and cycloaliphatic ethers, such as preferably cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones, such as preferably 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes, such as preferably 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as preferably 1-(3,3-dimethyl-cyctohexyl)-4-penten-1-one; 2,2-dimethyl-1-(2,4-dimethyl-3-cyclohexene-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl) ketone;

esters of cyclic alcohols, such as preferably 2-tert.-butylcyclohexyl acetate; 4-tert.-butylcyclohexyl acetate; 2-tert.-pentylcyclohexyl acetate; 4-tert.-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic alcohols, such as preferably 1-cyclohexylethyl crotonate;

esters of cycloaliphatic carboxylic acids, such as preferably allyl 3-cyclohexylpropionate; allylcyclohexyl oxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

aralicphatic alcohols, such as preferably benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as preferably benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, such as preferably 2-phenylethylmethyl ether; 2-phenyl ethyl isoamyl ether; 2-phenyl ethyl-1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as preferably benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 2-methyl-3-(4-isobutylphenyl) propanal; 3-(4-tert.-butylphenyl)propanal; cinnamaldehyde; alpha-butylcinnamaldehyde; alpha-amyicinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones, such as preferably acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)-ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and the esters thereof, such as preferably benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate;

nitrogenous aromatic compounds, such as preferably 2,4,6-trinitro-1,3-dimethyl-5-tert.-butylbenzene; 3,5-dinitro-2,6-dimethyl-4-tert.-butyl acetophenone; cinnamonitrile; 3-methyl-5-phenyl-2-pentenoic acid nitrile; 3-methyl-5-phenylpentanoic acid nitrile; methyl anthranilate; methyl-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde 6-isopropyl quinoline; 6-isobutyl quinoline; 6-sec.-butyl quinoline; 2-(3-phenylpropyl)pyridine; indole; skatole; 2-methoxy-3-isopropylpyrazine; 2-isobutyl-3-methoxypyrazine;

phenols, phenyl ethers and phenyl esters, such as preferably estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds, such as preferably 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as preferably 1,4-octanolide; 3-methyl-1,4-octanolide; 1,4-nonanolide; 14-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

If two, three or more further odoriferous and/or aroma substances are used in component (b) of the odoriferous and/or aroma substance compositions according to the invention, these may be selected from the extracts and/or from the individual odoriferous substances. If two, three or more further odoriferous and/or aroma substances are selected from the individual odoriferous substances, these may all be selected from one or more groups thereof.

An odoriferous or aroma substance composition according to the invention may be produced for example by mixing one, two, three, four or more compounds according to the invention of the formula (I) and/or formula (Ia) in component (a) with one, two, three or more further odoriferous or aroma substances of component (b). The compounds of component (a) are here regularly used in an amount which is sufficient to impart, modify and/or enhance an odor and/or flavor note of the musk type in the finished composition.

An odoriferous and/or aroma substance composition according to the invention preferably comprises a total quantity of the compounds according to the invention of the formula (I) and/or formula (Ia) of component (a) ranging from 0.00001 to 99.9 wt. %, preferably 0.001 to 70 wt. % and particularly preferably 0.01 to 50 wt. %, in each case relative to the total quantity of the odoriferous and/or aroma substance composition.

If one, two, three, four or more compounds according to the invention of the formula (I) and/or formula (Ia) are used with the purpose of imparting radiance, roundness and/or harmony to an odoriferous and/or aroma substance composition according to the invention and/or of enhancing specific odor and/or flavor notes of further odoriferous and/or aroma substances, the total quantity of component (a) is conventionally comparatively low and preferably in the range from 0.01 to 5 wt. %, particularly preferably in the range from 0.1 to 2 wt. %, in each case relative to the total quantity of the odoriferous and/or aroma substance composition. If, within the preferred concentration ranges, a comparatively low concentration is selected for one or more compounds according to the invention of the formula (I) and/or formula (Ia), in many cases, depending on the further components and the total quantity thereof in the respective composition, the above-stated intrinsic odor or flavor notes of the one, two or more compounds according to the invention of the formula (I) and/or formula (Ia) are not yet imparted.

Where the description of the invention, in particular below, but also above, refers to odoriferous and/or aroma substance compositions (according to the invention), these also include all the preferred developments thereof.

With regard to the third and fourth aspects of the present invention, perfumed product and aromatized product, one, two, three, four or more compounds according to the invention of the formula (I) and/or formula (Ia) and/or one, two, three or more odoriferous and/or aroma substance compositions according to the invention, in particular also according to the preferred developments, are conventionally used in quantities used in which the total quantity of the compounds of the formula (I) and/or formula (Ia) is organoleptically effective.

Preferably, a perfumed or aromatized product according to the invention comprises a total quantity of one, two, three, four or more compounds according to the invention of the formula (I) and/or formula (Ia), in particular also in component (a) of the odoriferous and/or aroma substance composition according to the invention, which is sufficient to impart, modify and/or enhance an odor and/or flavor with one, a plurality of or all of the musk-like notes in the product.

A preferred perfumed or aromatized product is characterized in that the product comprises a total quantity of one or more compounds according to the invention of formula (I) and/or formula (Ia), in particular in component (a) of an odoriferous and/or aroma substance composition according to the invention, which is sufficient to impart to this product a radiance, roundness and/or harmony and/or to enhance odor and/or flavor notes of a further odoriferous and/or aroma substance or two, three or more further odoriferous and/or aroma substances of the respective product.

Preferred perfumed or aromatized products according to the invention comprise in component (b) of the product according to the invention odoriferous and/or aroma substance compositions as have also in particular been described above as preferred developments for this purpose.

Preferred perfumed cosmetics or domestic products are selected from the group consisting of perfume extracts, eaux de parfum, eaux de toilette, shaving lotions, eaux de cologne, pre-shave products, splash colognes, perfumed tissue wipes, acidic, alkaline and neutral cleaning agents, preferably selected from the group consisting of floor cleaners, window cleaners, dishwashing detergents, bath and sanitary cleaners, scouring cream, solid or liquid toilet cleaners, pulverulent or foam carpet cleaners, textile fresheners, ironing aids, liquid detergents, pulverulent detergents, laundry pretreatment agents, laundry rinse conditioners, laundry soaps and laundry tablets, disinfectants, surface disinfectants, air fresheners in liquid or gel form or applied to a solid carrier, aerosol sprays, waxes and polishes preferably selected from the group consisting of furniture polishes, floor waxes and shoe polishes, bodycare products preferably selected from the group consisting of solid and liquid soaps, shower gels, shampoos, shaving soaps, shaving foams, bath oils and cosmetic emulsions of the oil-in-water, water-in-oil and water-in-oil-in-water type preferably selected from the group consisting of skin creams and lotions, face creams and lotions, sunscreen creams and lotions, after-sun creams and lotions, hand creams and lotions, foot creams and lotions, depilatory creams and lotions, after-shave creams and lotions, tanning: creams and lotions, hair care products preferably selected from the group consisting of hair sprays, hair gels, strengthening hair lotions, hair rinses, permanent and semi-permanent hair dyes, hair styling agents preferably selected from the group consisting of cold waving and hair smoothing products; hair tonics, hair creams and lotions, deodorants and antiperspirants preferably selected from the group consisting of underarm sprays, roll-ons, deodorant sticks and deodorant creams, decorative cosmetic products preferably selected from the group consisting of eyeshadows, nail varnish, make-up products, lipstick and mascara, candles, lamp oils, incense sticks, insecticides, repellents and propellants.

Preferred aromatized products, which are consumed for nutrition or pleasure, together with semifinished products thereof or seasoning mixtures are preferably selected from the group consisting of bakery products preferably selected from the group consisting of bread, dry biscuits, cakes and other pastry products, confectionery preferably selected from the group consisting of chocolate, chocolate bar products, other bar products, fruit gums, hard and soft caramels, chewing gum, alcoholic or non-alcoholic beverages preferably selected from the group consisting of coffee, tea, wine, beverages containing wine, beer, beverages containing beer, liqueurs, spirits, brandies, fruit-containing carbonated beverages, isotonic beverages, soft drinks, nectars, fruit and vegetable juices and fruit or vegetable juice preparations, instant beverages preferably selected from the group consisting of instant cocoa beverages, instant tea beverages and instant coffee beverages, meat products preferably selected from the group consisting of ham, fresh or cured sausage preparations and spiced or marinated fresh or cured meat products, eggs or egg products preferably selected from the group consisting of dried egg, egg white and egg yolk, cereal products preferably selected from the group consisting of breakfast cereals, muesli bars and precooked ready rice products, dairy products preferably selected from the group consisting of milk beverages, milk ice cream, yoghurt, kefir, curd cheese, soft cheese, hard cheese, dried milk powder, whey, butter, buttermilk and partially or fully hydrolyzed milk protein-containing products, products made from soy protein or other soybean fractions preferably selected from the group consisting of soy milk and products made therefrom, soy lecithin-containing preparations, fermented products such as tofu or tempe or products made therefrom and soy sauces, fruit preparations preferably selected from the group consisting of jams, fruit ice cream, fruit sauces and fruit fillings, vegetable preparations preferably selected from the group consisting of ketchup, sauces, dried vegetables, deep-frozen vegetables, precooked vegetables, pickled vegetables and preserved vegetables, snack articles preferably selected from the group consisting of baked or fried potato chips or potato dough products, bread dough products and maize- or peanut-based extrudates, fat- or oil-based products or emulsions thereof preferably selected from the group consisting of mayonnaise, remoulade, dressings and seasoning preparations, other ready-to-serve meals and soups preferably selected from the group consisting of dried soups, instant soups, precooked soups, spices, seasoning mixtures and powdered seasonings, which are for example used in snack food applications.

According to a preferred use according to the invention, one or more compounds according to the invention of the formula (I) and/or formula (Ia) are used as odoriferous and/or aroma substances preferably with musk-like notes, more preferably in odoriferous and/or aroma substance compositions according to the invention or perfumed or aromatized products according to the invention.

According to a further preferred development, one, two, three, four or more compounds according to the invention of the formula (I) and/or formula (Ia) are used for imparting, modifying and/or enhancing an odor or flavor with one, a plurality of or all of the musk-like notes.

According to a further preferred development, one, two, three, four or more compounds according to the invention of the formula (I) and/or formula (Ia) are used as a booster, preferably in an odoriferous and/or aroma substance composition according to the invention and the preferred developments thereof.

According to a further preferred development, one, two, three, four or more compounds according to the invention of the formula (I) and/or formula (Ia) are used on skin, hair and/or textile fibers to increase the substantivity of further odoriferous and/or aroma substances, preferably in component (b) of an odoriferous and/or aroma substance composition according to the invention together also with the preferred developments thereof.

According to a further preferred development, one, two, three, four or more compounds according to the invention of the formula (I) and/or formula (Ia) are used to increase the retention of further odoriferous and/or aroma substances, preferably in component (b) of an odoriferous and/or aroma substance composition according to the invention together also with the preferred developments thereof.

According to a further preferred development, one, two, three, four or more compounds according to the invention of the formula (I) and/or formula (Ia) are used to impart radiance, roundness and/or harmony to an odoriferous and/or aroma substance composition, in particular also to the preferred developments thereof and/or to enhance existing odor and/or flavor notes in an odoriferous and/or aroma substance composition according to the invention, in particular also the preferred developments thereof.

The production of compounds according to the invention of the formula (I) may proceed by means of per se known reactions and methods (Jerry March, Advanced Organic Chemistry: Reactions, Mechanisms and Structure, 4th Ed., John Wiley and Sons, 1992 and Richard C. Larock, Comprehensive Organic Transformations: A Guide to Functional Group Preparations, VCH Verlag, 1989) with one or more of the following steps:

a) epoxidation of a compound of the formula (II) to yield a corresponding compound of the formula (III)

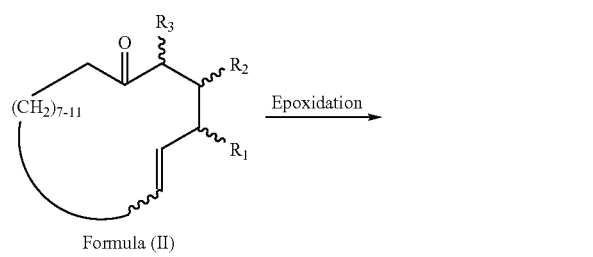

wherein $R_1$, $R_2$ and $R_3$ have the above-stated meanings, b) subsequent reduction of the corresponding compound of the formula (III) to yield a corresponding compound of the formula (IV)

wherein $R_1$, $R_2$ and $R_3$ have the above-stated meanings, c) subsequent cyclization of the corresponding compound of the formula (IV) to yield a corresponding compound of the formula (V)

wherein $R_1$, $R_2$ and $R_3$ have the above-stated meanings and d) subsequent oxidation of the corresponding compound of the formula (V) to yield a corresponding compound of the formula (I)

-continued

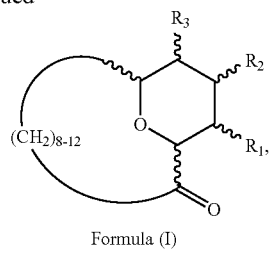

Formula (I)

wherein $R_1$, $R_2$ and $R_3$ have the above-stated meanings.

The production of compounds according to the invention of the formula (I) may proceed by means of per se known reactions and methods (Jerry March, Advanced Organic Chemistry. Reactions, Mechanisms and Structure, 4th Ed., John Wiley and Sons, 1992 and Richard C. Larock, Comprehensive Organic Transformations: A Guide to Functional Group Preparations, VCH Verlag, 1989).

Below, the production is described of 17-oxa-bicyclo[11.3.1]heptadecan-2-one, and 14-methyl-16-oxa-bicyclo[10.3.1]hexadecan-2-one, as exemplary examples for the production of a compound of the formula (I):

17-Oxa-bicyclo[11.3.1]heptadecan-2-one

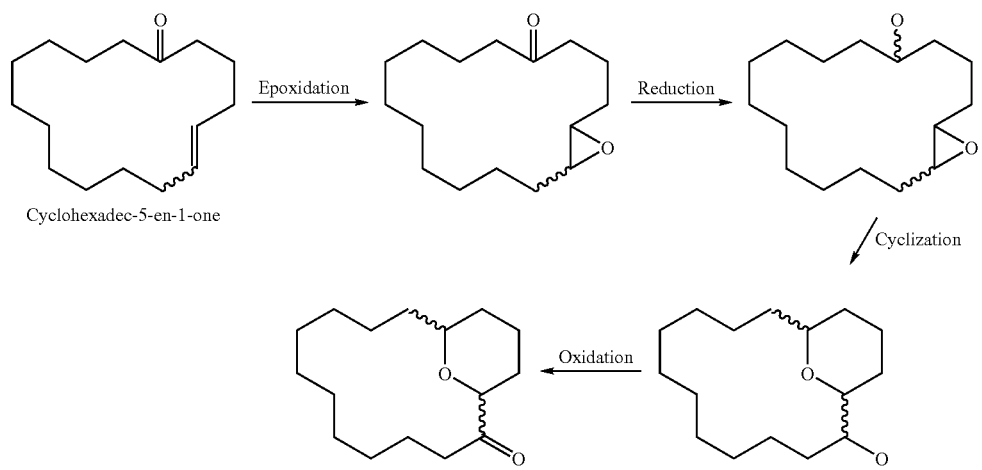

The corresponding further compounds of the formula (I) may be produced from cyclotetradec-5-en-1-one, cyclopentadec-5-en-1-one, cycloheptadec-5-en-1-one and cyclooctadec-5-en-1-one in a manner similar to this production.

14-Methyl-16-oxa-bicyclo[10.3.1]hexadecan-2-one

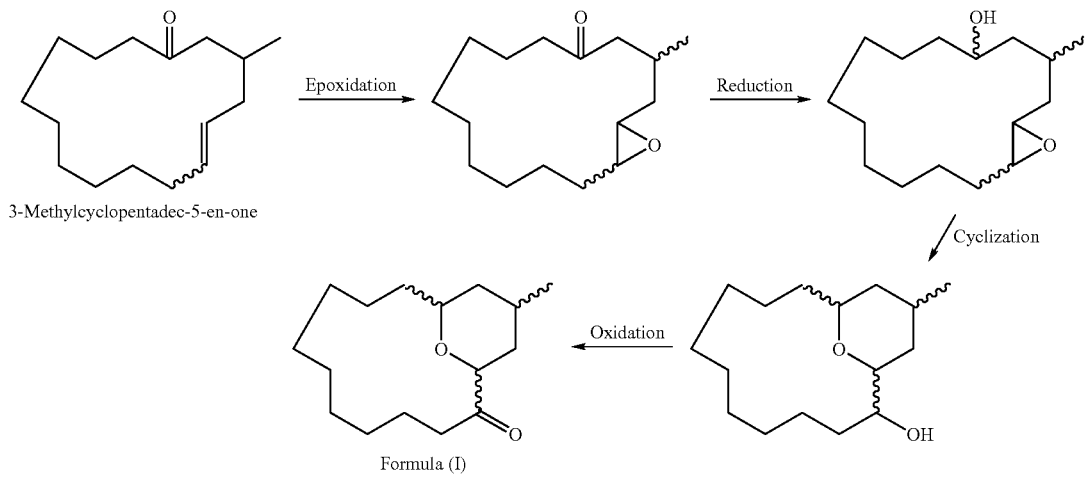

The corresponding further compounds of the formula (I) may be produced from 2-methyl-cyclopentadec-5-en-1-one, 3-methyl-cyclopentadec-5-en-1-one and 4-methyl-cyclopentadec-5-en-1-one in a manner similar to this production.

The production of compounds according to the invention of the formula (Ia) may proceed by means of per se known reactions and methods (Jerry March, Advanced Organic Chemistry: Reactions, Mechanisms and Structure, 4th Ed, John Wiley and Sons, 1992 and Richard C. Larock, Comprehensive Organic Transformations: A Guide to Functional Group Preparations, VCH Verlag, 1989) with one or more of the following steps:

a) reduction of a compound of the formula (IIIa) to yield a corresponding compound of the formula (IIIa)

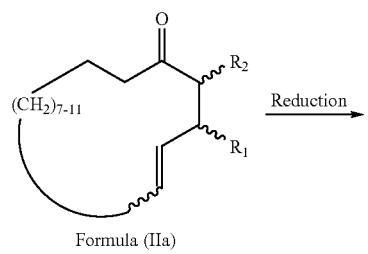

Formula (IIa)

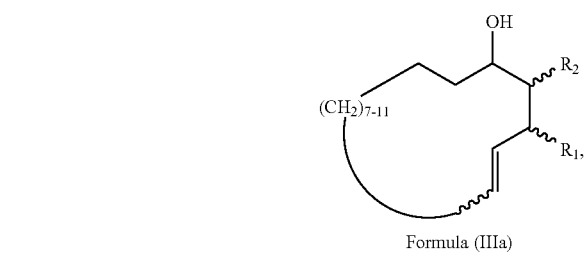

Formula (IIIa)

wherein $R_1$ and $R_2$ have the above-stated meanings, b) subsequent epoxidation of the corresponding compound of the formula (IIIa) to yield a corresponding compound of the formula (IVa)

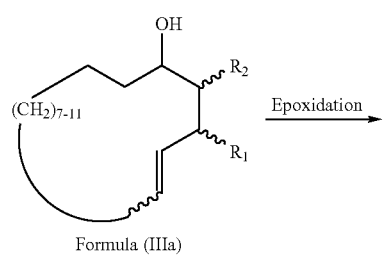

Formula (IIIa)

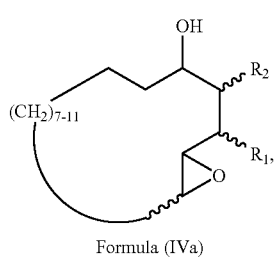

Formula (IVa)

wherein $R_1$ and $R_2$ have the above-stated meanings, c) subsequent cyclization of the corresponding compound of the formula (IVa) to yield a corresponding compound of the formula (Va)

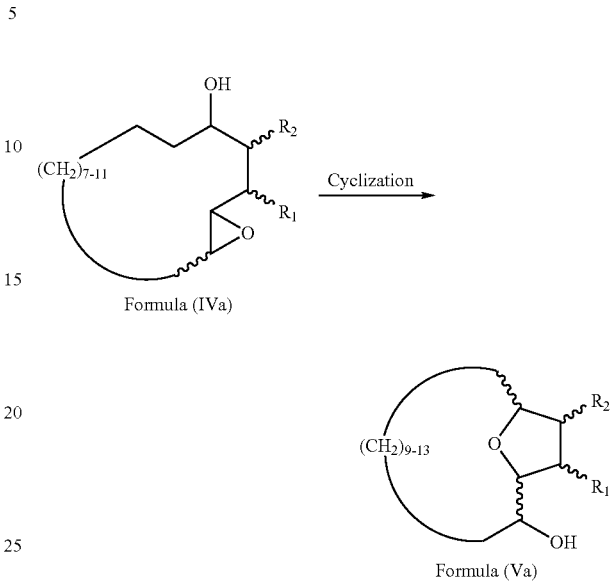

Formula (IVa)

Formula (Va)

wherein $R_1$ and $R_2$ have the above-stated meanings and d) subsequent oxidation of the corresponding compound of the formula (Va) to yield a corresponding compound of the formula (Ia)

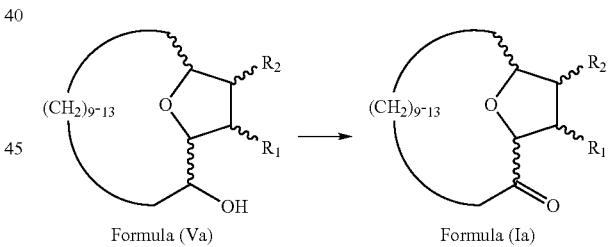

Formula (Va)            Formula (Ia)

wherein $R_1$ and $R_2$ have the above-stated meanings.

The production of compounds according to the invention of the formula (I) may proceed by means of per se known reactions and methods (Jerry March, Advanced Organic Chemistry: Reactions, Mechanisms and Structure, 4th Ed., John Wiley and Sons, 1992 and Richard C. Larock, Comprehensive Organic Transformations: A Guide to Functional Group Preparations, VCH Verlag, 1989).

Below, the production is described of 16-oxa-bicyclo[11.2.1]hexadecan-2-one, and 15-methyl-16-oxa-bicyclo[11.2.1]hexadecan-2-one, as exemplary examples for the production of a compound of the formula (Ia):

16-Oxa-bicyclo[11.2.1]hexadecan-2-one

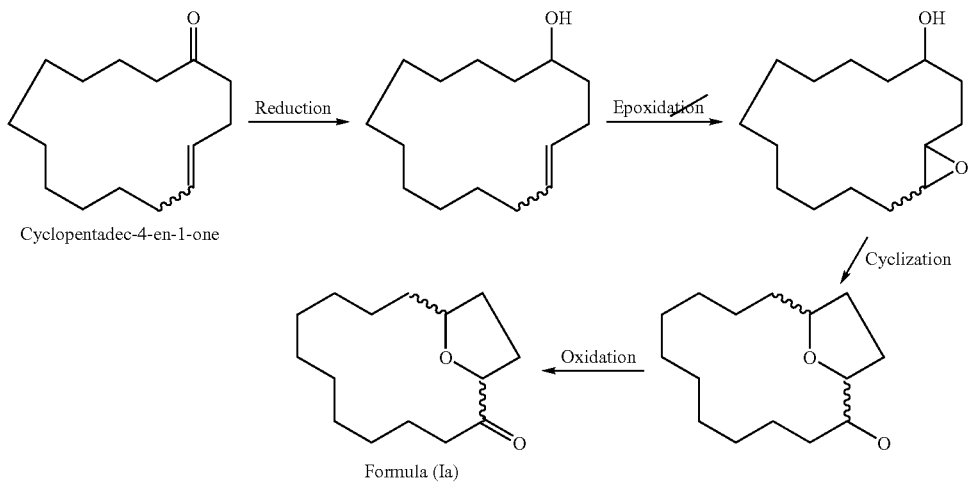

Formula (Ia)

The corresponding further compounds of the formula (Ia) may be produced from cyclotetradec-4-en-1-one, cyclohexadec-4-en-1-one, cycloheptadec-4-en-1-one and cyclooctadec-4-en-1-one in a manner similar to this production.

15-Methyl-16-oxa-bicyclo[11.2.1]hexadecan-2-one

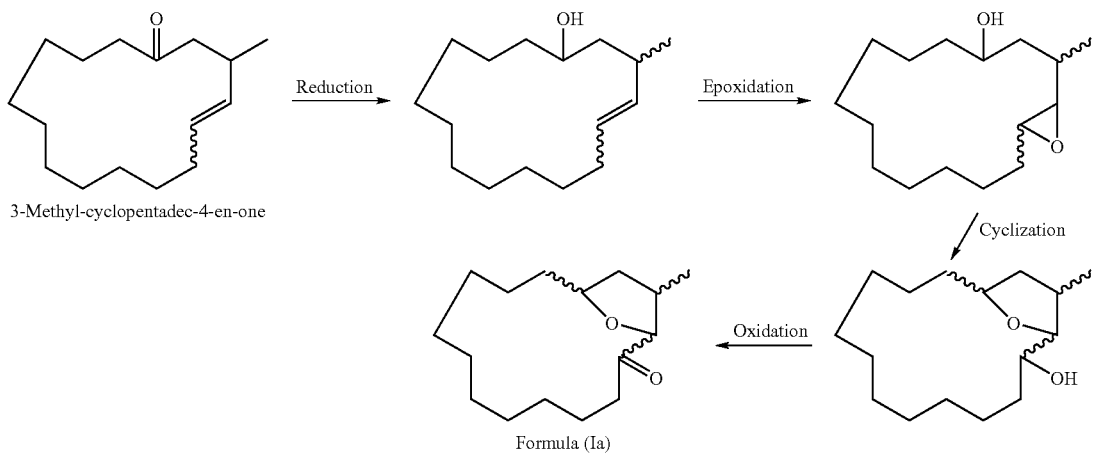

Formula (Ia)

The corresponding further compounds of the formula (Ia) may be produced from 2-methyl-cyclopentadec-4-en-1-one in a manner similar to this production.

Alternatively, compounds of the formula (I) and of the formula (Ia) may be produced simultaneously by selecting suitable educts and adaptation of one of the above-described production methods.

One, two, three, four or more compounds according to the invention of the formula (I) and formula (Ia) or one or more odoriferous and/or aroma substance compositions according to the invention, which contain one, two, three, four or more compounds according to the invention of the formula (I) and/or of the formula (Ia), may conventionally be used in concentrated form, in solutions or in the form as modified above for the production of perfumed cosmetics or domestic products according to the invention, wherein these products are preferably selected from the group consisting of:

perfume extracts, eaux de parfum, eaux de toilette, shaving lotions, eaux de cologne, pre-shave products, splash colognes, perfumed tissue wipes, acidic, alkaline and neutral cleaning agents, preferably selected from the group consisting of floor cleaners, window cleaners, dishwashing detergents, bath and sanitary cleaners, scouring cream, solid or liquid toilet cleaners, pulveruient or foam carpet cleaners, textile fresheners, ironing aids, liquid detergents, pulveruient detergents, laundry pretreatment agents, laundry rinse conditioners, laundry soaps and laundry tablets, disinfectants, surface disinfectants, air fresheners in liquid or gel form or applied to a solid carrier, aerosol sprays, waxes and polishes preferably selected from the group consisting of furniture polishes, floor waxes and shoe polishes, bodycare products preferably selected from the group consisting of solid and liquid soaps, shower gels, shampoos, shaving soaps, shaving foams, bath oils and cosmetic emulsions of the oil-in-water, water-in-oil and water-in-oil-in-water type preferably selected from the group consisting of skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products preferably selected from the group consisting of hair sprays, hair gels, strengthening hair lotions, hair rinses, permanent and semi-permanent hair dyes, hair styling agents preferably selected from the group consisting of cold waving and hair smoothing products; hair tonics, hair creams and lotions, deodorants and antiperspirants preferably selected from the group consisting of underarm sprays, roll-ons, deodorant sticks and deodorant creams, decorative cosmetic products preferably selected from the group consisting of eyeshadows, nail varnish, make-up products, lipstick and mascara, candies, lamp oils, incense sticks, insecticides, repellents, and propellants.

The compounds according to the invention of the formula (I) and/or (Ia) may be incorporated into articles which are aromatized or are to be aromatized, in particular into preparations consumed for nutrition or pleasure or used for oral care, semifinished mixtures and seasoning mixtures.

The preparations according to the invention consumed for nutrition or pleasure are preferably selected from the group consisting of:

bakery products preferably selected from the group consisting of bread, dry biscuits, cakes and other pastry products, confectionery preferably selected from the group consisting of chocolate, chocolate bar products, other bar products, fruit gums, hard and soft caramels, chewing gum, alcoholic or non-alcoholic beverages preferably selected from the group consisting of coffee, tea, wine, beverages containing wine, beer, beverages containing beer, liqueurs, spirits, brandies, fruit-containing carbonated beverages, isotonic beverages, soft drinks, nectars, fruit and vegetable juices, fruit or vegetable juice preparations, instant beverages preferably selected from the group consisting of instant cocoa beverages, instant tea beverages and instant coffee beverages, meat products preferably selected from the group consisting of ham, fresh or cured sausage preparations and spiced or marinated fresh or cured meat products, eggs or egg products preferably selected from the group consisting of dried egg, egg white and egg yolk, cereal products preferably selected from the group consisting of breakfast cereals, muesli bars and precooked ready rice products, dairy products preferably selected from the group consisting of milk beverages, milk ice cream, yogurt, kefir, curd cheese, soft cheese, hard cheese, dried milk powder, whey, butter, buttermilk and partially or fully hydrolyzed milk protein-containing products, products made from soy protein or other soybean fractions preferably selected from the group consisting of soy milk and products made therefrom, soy lecithin-containing preparations, fermented products such as tofu or tempe or products made therefrom and soy sauces, fruit preparations preferably selected from the group consisting of jams, fruit ice cream, fruit sauces and fruit fillings, vegetable preparations preferably selected from the group consisting of ketchup, sauces, dried vegetables, deep-frozen vegetables, precooked vegetables, pickled vegetables and preserved vegetables, snack articles preferably selected from the group consisting of baked or fried potato chips or potato dough products, bread dough products and maize- or peanut-based extrudates, fat- or oil-based products or emulsions thereof preferably selected from the group consisting of mayonnaise, remoulade, dressings and seasoning preparations, other ready-to-serve meals and soups preferably selected from the group consisting of dried soups, instant soups, precooked soups, spices, seasoning mixtures and powdered seasonings, which are for example used in snack food applications.

Aromatized products according to the invention may in particular serve as a semifinished product for the production of further preparations consumed for nutrition or pleasure, preferably in spray-dried form. Aromatized semifinished products according to the invention may also be nutritional supplements, preferably in the form of capsules, tablets, preferably uncoated and coated tablets (for example coatings resistant to gastric juices), sugar-coated tablets, granules, pellets, mixtures of solids, dispersions in liquid phases, emulsions, powders, solutions, pastes or other swallowable or chewable preparations.

The aromatized products according to the invention for oral care purposes are preferably selected from oral and/or dental care products such as toothpastes, tooth gels, tooth powders, mouthwashes, chewing gums and other oral care products, Conventional active ingredients, basic materials, auxiliary substances and additives for aromatized products according to the invention consumed for nutrition or pleasure or used for oral care may be present in quantities of 5 to 99.999999 wt. %, preferably of 10 to 80 wt. %, relative to the total weight of the product. The aromatized products may furthermore comprise water in a quantity of up to 99.999999 wt. %, preferably of 5 to 80 wt. %, relative to the total weight of the product.

Aromatized products according to the invention, comprising compounds according to the invention of the formula (I) and/or the formula (Ia) are produced according to a preferred development by incorporating one or more compounds according to the invention of the formula (I) and/or the formula (Ia) conventionally as a solid substance, as a solution (for example in ethanol, water or 1,2-propylene glycol) or in the form of a mixture with a solid or liquid carrier (for example maltodextrin, starch, silica gel), further odoriferous and/or aroma substances and optionally further auxiliaries and/or stabilizers (preferably natural or artificial polysaccharides and/or vegetable gums such as modified starches or gum arabic) into a base preparation consumed for nutrition or for pleasure or used for oral care. Advantageously, preparations according to the invention assuming solution and/or suspension or emulsion form may also be converted by spray drying into a solid aromatized semifinished product according to the invention.

The spray-dried solid aromatized products according to the invention are, as semifinished products, particularly well suited to the production of further aromatized products according to the invention. The preferred spray-dried, solid, aromatized products according to the invention preferably contain 50 to 95 wt. % carriers, in particular maltodextrin and/or starch, 5 to 40% auxiliary substances, preferably natural or artificial polysaccharides and/or vegetable gums such as modified starches or gum arabic.

According to a further preferred embodiment, aromatized products according to the invention may be produced by incorporating firstly one, two, three, four or more compounds according to the invention of the formula (I) and/or of the formula (Ia) and optionally further constituents of the aromatized product according to the invention, preferably one, two, three or more further odoriferous and/or aroma substances, into emulsions, into liposomes, for example starting from phosphatidyl choline, into microspheres, into nanospheres or also into capsules, granules or extrudates prepared from a matrix suitable for foodstuffs and products consumed for pleasure, for example prepared from starch, starch derivatives (for example modified starch), cellulose or cellulose derivatives (for example hydroxypropylcellulose), other polysaccharides (for example dextrin, alginate, curdlan, carageenan, chitin, chitosan, pullulan), natural fats, natural waxes (for example beeswax, carnauba wax) or from proteins, for example gelatin or other natural products (for example shellac). In said embodiment, depending on the matrix, the products may be obtained by spray drying, spray granulation, melt granulation, coacervation, coagulation, extrusion, melt extrusion, emulsion methods, coating or other suitable encapsulation methods and optionally a suitable combination of the above-stated methods. In a further preferred production method for a preparation according to the invention, one or more aldehydes of type (I) and/or (II) are initially complexed with one or more complexing agents, for example with cyclodextrins or cyclodextrin derivatives, preferably α- or β-cyclodextrin, and used in this complexed form.

Preference is given to a preparation according to the invention in which the matrix is so selected that one, two, three, four or more compounds according to the invention of the formula (I) and/or formula (Ia) are released by the matrix in delayed manner, such that a long-lasting organoleptic action is achieved. A fat, wax, polysaccharide or protein matrix is particularly preferred in this respect.

The further constituents for preparations according to the invention consumed for nutrition or pleasure may comprise conventional basic materials, auxiliary substances and additives for foodstuffs or products consumed for pleasure, preferably one, two, three, four or more of these constituents are selected from the group consisting of water, mixtures of fresh or processed, plant or animal basic or raw materials (for example raw, roasted, dried, fermented, smoked and/or boiled meat, bone, cartilage, fish, vegetables, fruit, herbs, nuts, vegetable or fruit juices or pastes or mixtures thereof), digestible or non-digestible carbohydrates (for example sucrose, maltose, fructose, glucose, dextrins, amylose, amylopectin, inulin, xylans, cellulose, tagatose), sugar alcohols (for example sorbitol, erythritol), natural or hardened fats (for example tallow, lard, palm fat, coconut oil, hardened vegetable fat), oils (for example sunflower oil, peanut oil, maize germ oil, olive oil, fish oil, soya oil, sesame oil), fatty acids or the salts thereof (for example potassium stearate) proteinogenic or non-proteinogenic amino acids and related compounds (for example γ-aminobutyric acid, taurine), peptides (for example glutathione), native or processed proteins (for example gelatin), enzymes (for example peptidases), nucleic acids, nucleotides, flavor-correcting agents for unpleasant flavor impressions, further flavor modulators for further, generally not unpleasant flavor impressions, other flavor-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carageenan, alginate), preservatives (for example benzoic acid, sorbic acid), antioxidants (for example tocopherol, ascorbic acid), chelating agents (for example citric acid), organic or inorganic acidulants (for example malic acid, acetic acid, citric acid, tartaric acid, phosphoric acid), bitter substances (for example quinine, caffeine, limonin, amarogentin, humulone, lupulone, catechins, tannins), mineral salts (for example sodium chloride, potassium chloride, magnesium chloride, sodium phosphates), substances preventing enzymatic browning (for example sulfite, ascorbic acid), essential oils, plant extracts, natural or synthetic dyes or coloring pigments (for example carotenoids, flavonoids, anthocyans, chlorophyll and the derivatives thereof), spices, trigeminally active substances or plant extracts containing such trigeminally active substances, synthetic, natural or nature-identical aroma substances or odoriferous substances and odor-correcting agents.

Dental care products (as the basis for aromatized products for oral care purposes), which contain one or more compounds according to the invention of the formula (I) and/or formula (Ia) and/or contain odoriferous and/or aroma substances according to the invention, generally comprise an abrasive system (abrasive or polishing agent), wherein one, two, three or more constituents of the abrasive system are preferably selected from the group consisting of silicas, calcium carbonates, calcium phosphates, aluminum oxides and/or hydroxyapatites, surface-active substances, such as for example sodium lauryl sulfate, sodium iauryl sarcosinate and/or cocamidopropyl betaine, humectants such as for example glycerol and/or sorbitol, thickeners, such as for example carboxymethylcellulose, polyethylene glycols, carrageenan and/or Laponite®, sweeteners, such as for example saccharin, flavor-correcting agents for unpleasant flavor impressions, flavor-correcting agents for further, generally not unpleasant flavor impressions, flavor-modulating substances (for example inositol phosphate, nucleotides, such as guanosine monophosphate, adenosine monophosphate or other substances such as sodium glutamate or 2-phenoxypropionic acid), cooling active ingredients, such as for example menthol, menthol derivatives (for example L-menthol, L-menthyl lactate, L-menthyl alkylcarbonates, menthone ketals, menthane carboxamides), 2,2,2-trialkylacetamides (for example 2,2-diisopropylpropionic acid methylamide), icilin and icilin derivatives, stabilizers and active ingredients, such as for example sodium fluoride, sodium monofluorophosphate, tin difluoride, quaternary ammonium fluorides, zinc citrate, zinc sulfate, tin pyrophosphate, tin dichloride, blends of different pyrophosphates, triclosan, cetylpyridinium chloride, aluminum lactate, potassium citrate, potassium nitrate, potassium chloride, strontium chloride, hydrogen peroxide, aromas and/or sodium bicarbonate or odor-correcting agents.

Chewing gums (as a further example of aromatized products for oral care purposes) which contain one or more aldehydes of type (I) and/or (II) generally comprise a chewing gum base, i.e. a chewable mass which becomes plastic on chewing, sugars of various kinds, sugar substitutes, other sweet-tasting substances, sugar alcohols, flavor-correcting agents for unpleasant flavor impressions, other flavor modulators for further, generally not unpleasant flavor impressions, flavor-modulating substances (for example inositol phosphate, nucleotides such as guanosine monophosphate, adenosine monophosphate or other substances such as sodium glutamate or 2-phenoxypropionic acid), humectants, thickeners, emulsifiers, aromas and stabilizers or flavor-correcting agents.

Preferably, perfumed or aromatized products according to the invention may contain, in addition to one or more compounds according to the invention of the formula (I) and/or formula (Ia), one, two, three, four or more odoriferous and/or aroma substance compositions according to the invention, in order further to round off and/or refine the flavor and/or odor of the perfumed or aromatized product. Suitable (additional) odoriferous and/or aroma substance compositions according to the invention preferably contain one or more synthetic, natural and/or nature-identical aroma, odoriferous and/or flavor substances and further preferably one or more suitable auxiliary substances and carriers.

The invention is illustrated in greater detail below with reference to Examples. Unless otherwise stated, all stated values relate to weight.

EXAMPLE 1

Production of 17-oxa-bicyclo[11.3.1]heptadecan-2-one as a compound of the formula (I)

1st Stage: Epoxidation 23.6 g (0.1 mol) of cyclohexadec-5-en-1-one in 250 ml of methylene chloride were initially introduced into a 500 ml stirrer with 25 g of sodium acetate. Then 23.4 g (0.12 mol) of 38% peracetic acid were added dropwise with stirring and cooling at 18-25° C. over a period of 2 hours. Then stirring was continued for 4 hours at room temperature. The reaction solution was washed with water, iron(II) sulfate solution and soda solution and evaporated. Crude yield: 24.3 g.

GC evaluation (20 m ZB-WAX, internal diameter 0.18 µm/60-9-220° C. programmed-temperature vaporization system)

The crude product was reacted in the 2nd stage without further purification.

2nd Stage: Reduction

In a 250 ml stirrer, 24.3 g of crude product from stage 1 in 100 ml of methanol were combined, with stirring and cooling at 20° C., with a solution of 5 g of water, 20 mg of NaOH and 1.3 g of sodium hydridoborate. Then stirring was continued for 4 h at 20° C. For working up, the methanol was removed in a rotary evaporator, the residue being combined with 100 g of toluene and 100 g of water. After separation of the phases, the organic phase was washed once with water and the toluene was removed. Crude yield: 24.3 g.

GC evaluation (20 m ZB-WAX, internal diameter 0.18 µm/60-9-220° C. programmed-temperature vaporization system)

The crude product was reacted in the 3rd stage without further purification.

3rd Stage: Cyclization

In a 250 ml stirrer, 24.3 g of crude product from stage 2 in 200 ml of toluene was combined with stirring at 20° C. with 25 mg of p-toluenesulfonic acid. Then stirring was continued for 4 h at 20° C. For working up, the reaction mixture was washed with sodium hydrogencarbonate solution. After separation of the phases, the organic phase was washed once with water and the toluene was removed. Crude yield: 24.2 g.

GC evaluation (20 m ZB-WAX, internal diameter 0.18 µm/60-9-220° C. programmed-temperature vaporization system)

The crude product was reacted in the 4th stage without further purification.

4th Stage: Oxidation

In a 2 l stirrer, 24.2 g of crude product from stage 3 were dissolved in 1000 ml of methylene chloride and combined with stirring at 20-25° C. with 56.8 g (0.15 mol) of pyridinium dichromate. Then stirring was continued for 4 h at 20° C. For working up, the reaction mixture was filtered over silica gel, washed with dilute sulfuric acid and sodium hydrogencarbonate solution and the methylene chloride was removed. Crude yield: 23.8 g (approx. 1:1 E/Z isomers).

GC evaluation (20 m ZB-WAX, internal diameter 0.18 µm/60-9-220° C. programmed-temperature vaporization system)

The crude product was purified using column chromatography.

The spectroscopic data were determined for the 17-oxa-bicyclo[11.3.1]heptadecan-2-one produced. The data for the E/Z isomers are stated below.

17-Oxa-bicyclo[11.3.1]heptadecan-2-one Z isomer $^1$H-NMR (CDCl$_3$, 400 MHz, TMS=0): 3.8 (J=11.4, J=2.4, 1H); 3.4 (J=11.3, J=9.8, J=2.2, 1H); 2.8 (1H); 2.2 (1H); 1.76-1.94 (3H); 1.20-1.75 (21H).

$^{13}$C-NMR (CDCl$_3$, 100 MHz): 212.8 (s), 81.9 (d), 77.5 (d), 38.4 (t), 35.2 (t), 31.9 (t), 26.9 (t), 26.7 (t), 26.3 (t), 25.8 (t), 25.7 (t),. 24.9 (t), 24.2 (t), 23.34 (t), 23.32 (t), 23.2 (t).

MS: m/z (%)=252 (14, M$^+$), 224 (8), 111 (12), 98 (32), 85 (36), 67 (42), 55 (100), 41 (96), 29 (37).

Odor Description, Z-Isomer: Weak Musk Odor, Slightly Leathery Animal Odor

17-Oxa-bicyclo[11.3.1]heptadecan-2-one E isomer $^1$H-NMR (CDCl$_3$, 400 MHz, TMS=0); 4.2(1H); 3.3 (J=9.6, J=4.1, J=2.3, 1H); 3.1 (J=17.2, J=11.0, J=5.6, 1H); 2.2 (J=17.2, J=5.0, J=0.7, 1H); 1.8-2.1 (1H); 1.1-1.8 (23H).

$^{13}$C-NMR (CDCl$_3$, 100 MHz): 212.9 (s), 78.2 (d), 72.5 (d), 36.5 (t), 34.4 (t), 31.4 (t), 25.9 (t), 25.44 (t), 25.43 (t), 24.6 (t), 24.0 (t), 23.9 (t), 23.8 (t), 23.1 (t), 20.5 (t), 19.7 (t).

MS: m/z (%)=252 (20, M$^+$), 224 (10), 111 (12), 98 (28), 85 (34), 67 (43), 55 (100), 41 (90), 29 (33).

Odor Description, E-Isomer: Very Strong Clean Musk Odor, Interesting Delicate Erogenous Fragrance Note, Very Natural Odor Impression.

EXAMPLE 2

Production of 14-methyl-16-oxa-bicyclo[10.3.1]hexadecan-2-one: as a compound of the formula (I)

1st Stage: Epoxidation 23.6 g (0.1 mol) of 3-methyl-cyclopentadec-5-en-1-one (concentrated by distillation from commercially obtainable 82% 3-methyl-cyclopentadec-5-en-1-one) in 250 ml of methylene chloride were initially introduced into a 500 ml stirrer with 25 g of sodium acetate. Then 23.4 g (0.12 mol) of 38% peracetic acid were added dropwise with stirring and cooling at 18-25° C. over a period of 2 hours. Then stirring was continued for 4 hours at room temperature. The reaction solution was washed with water, iron(II) sulfate solution and soda solution and evaporated. Crude yield: 24.9 g.

GC evaluation (20 m ZB-WAX, internal diameter 0.18 µm/60-9-220° C. programmed-temperature vaporization system)

The crude product was reacted in the 2nd stage without further purification.

2nd Stage: Reduction

In a 250 ml stirrer, 24.9 g of crude product from stage 1 in 100 ml of methanol were combined, with stirring and cooling at 20° C., with a solution of 5 g of water, 20 mg of NaOH and 1.3 g of sodium hydridoborate. Then stirring was continued for 4 h at 20° C. For working up, the methanol was removed in a rotary evaporator, the residue being combined with 100 g of toluene and 100 g of water. After separation of the phases, the organic phase was washed once with water and the toluene was removed. Crude yield: 24.6 g.

GC evaluation (20 m ZB-WAX, internal diameter 0.18 µm/60-9-220° C. programmed-temperature vaporization system)

The crude product was reacted in the 3rd stage without further purification.

3rd Stage: Cyclization

In a 250 ml stirrer, 24.6 g of crude product from stage 2 in 200 ml of toluene was combined with stirring at 20° C. with 25 mg of p-toluenesulfonic acid. Then stirring was continued for 4 h at 20° C. For working up, the reaction mixture was washed with sodium hydrogencarbonate solution. After separation of the phases, the organic phase was washed once with water and the toluene was removed. Crude yield: 24.4 g.

GC evaluation (20 m ZB-WAX, internal diameter 0.18 µm/60-9-220° C. programmed-temperature vaporization system)

The crude product was reacted in the 4th stage without further purification.

4th Stage: Oxidation

In a 2 l stirrer, 24.4 g of crude product from stage 3 were dissolved in 1000 ml of methylene chloride and combined with stirring at 20-25° C. with 56.8 g (0.15 mol) of pyridinium dichromate. Then stirring was continued for 4 h at 20° C. For working up, the reaction mixture was filtered over silica gel, washed with dilute sulfuric acid and sodium hydrogencarbonate solution and the methylene chloride was removed. Crude yield: 23.6 g (approx. 1:1 E/Z isomers).

GC evaluation (20 m ZB-WAX, internal diameter 0.18 µm/60-9-220° C. program med-temperature vaporization system)

The crude product was purified using column chromatography.

The spectroscopic data were determined for the 14-methyl-16-oxa-bicyclo[10.3.1]hexadecan-2-one produced. The isomer data are stated below.

14-Methyl-16-oxa-bicyclo[10.3.1]hexadecan-2-one

Isomer 1 Index 1862

MS: m/z (%)=252 (96, M$^+$), 180 (57), 99 (67), 97 (60), 81 (73), 71 (65), 68 (64), 55 (100), 41 (71).

Odor Description: Pleasant Mellow Musk-Like Odor

14-Methyl-16-oxa-bicyclo[10.3.1]hexadecan-2-one

Isomer 2 Index 1868

MS: m/z (%)=252 (86, M$^+$), 180 (60), 99 (69), 97 (62), 81 (76), 71 (66), 68 (66), 55 (100), 41 (72).

Odor Description: Pleasant Mellow Musk-Like Odor

14-Methyl-16-oxa-bicyclo[10.3.1]hexadecan-2-one

Isomer 3 Index 1891

MS: m/z (%)=252 (75, M$^+$), 180 (53), 99 (74), 97 (60), 81 (72), 71 (65), 68 (63), 55 (100), 41 (73),

Odor Description: Pleasant Mellow Musk-Like Odor

14-Methyl-16-oxa-bicyclol[10.3.1]hexadecan-2-one

Isomer 4 Index 1907

MS: m/z (%)=252 (77, M$^+$), 180 (56), 99 (75), 97 (62), 81 (72), 71 (65), 68 (63), 55 (100), 41 (70).

Odor Description: Pleasant Mellow Musk-Like Odor

EXAMPLE 3

Production of 16-oxa-bicyclo[11.2.1]hexadecan-2-one as a compound of the formula (Ia)

1st Stage: Reduction 22.2 g (0.1 mol) of cyclopentadec-4-en-1-one in 100 ml of methanol were initially introduced with stirring and cooling at 20° C. into a 250 ml stirrer with a solution of 5 g of water, 20 mg of NaOH and 1.3 g of sodium hydridoborate. Then stirring was continued for 4 h at 20° C. For working up, the methanol was removed in a rotary evaporator, the residue being combined with 100 g of toluene and 100 g of water. After separation of the phases, the organic phase was washed once with water and the toluene was removed. Crude yield: 23.3 g.

GC evaluation (20 m ZB-WAX, internal diameter 0.18 µm/60-9-220° C. programmed-temperature vaporization system)

The crude product was reacted in the 2nd stage without further purification.

2nd Stage: Epoxidation 23.3 g of crude product from stage 1 in 250 ml of methylene chloride were initially introduced into a 500 ml stirrer with 25 g of sodium acetate. Then 23.4 g (0.12 mol) of 38% peracetic acid were added dropwise with stirring and cooling at 18-25° C. over a period of 2 hours. Then stirring was continued for 4 hours at room temperature. The reaction solution was washed with water, iron(II) sulfate solution and soda solution and evaporated. Crude yield. 24.9 g.

GC evaluation (20 m ZB-WAX, internal diameter 0.18 µm/60-9-220° C. programmed-temperature vaporization system)

The crude product was reacted in the 3rd stage without further purification.

3rd Stage: Cyclization

In a 250 ml stirrer, 24.9 g of crude product from stage 2 in 200 ml toluene was combined with stirring at 20° C. with 25 mg of p-toluenesulfonic acid. Then stirring was continued for 4 h at 20° C. For working up, the reaction mixture was washed with sodium hydrogencarbonate solution. After separation of the phases, the organic phase was washed once with water and the toluene was removed. Crude yield: 24.2 g.

GC evaluation (20 m ZB-WAX, internal diameter 0.18 µm/60-9-220° C. programmed-temperature vaporization system)

The crude product was reacted in the 4th stage without further purification.

4th Stage: Oxidation

In a 2 l stirrer, 24.2 g of crude product from stage 3 were dissolved in 1000 ml of methylene chloride and combined with stirring at 20-25° C. with 56.8 g (0.15 mol) of pyridinium dichromate. Then stirring was continued for 4 h at 20° C. For working up, the reaction mixture was filtered over silica gel, washed with dilute sulfuric acid and sodium hydrogencarbonate solution and the methylene chloride was removed. Crude yield: 23.8 g (approx. 1:1 E/Z isomers).

GC evaluation (20 m ZB-WAX, internal diameter 0.18 µm/60-9-220° C. programmed-temperature vaporization system)

The crude product was purified using column chromatography.

The spectroscopic data were determined for the 16-oxa-bicyclo[11.2.1]hexadecan-2-one produced. The data for the E/Z isomers are stated below.

16-Oxa-bicyclo[11.2.1]hexadecan-2-one Z isomer $^1$H-NMR (CDCl$_3$, 400 MHz, TMS=0): 4.2 (J=8, J=6.9, 1H); 4.0 (J=8.6, J=7.3, J=6.2, J=2.7, 1H); 2.7 (1H); 2.5 (1H); 2.1 (1H); 1.50-1.78 (3H); 1.20-1.78 (18H).

$^{13}$C-NMR (CDCl$_3$, 100 MHz): 214.1 (s), 84.1 (d), 71.5 (d), 37.8 (t), 34.1 (t), 31.4 (t), 28.4 (t), 27.1 (t), 26.9 (t), 25.8 (t),. 25.6 (t), 25.3 (t), 25.25 (t), 24.4 (t), 22.8 (t).

MS: m/z (%) 238 (20, M$^+$), 210 (21), 166 (7), 126 (11), 111 (18), 97 (47), 84 (68), 71 (87), 55 (100), 41(85), 29(34).

Odor Description, E-Isomer: Very Strong Clean Musk Odor, Interesting Delicate Erogenous Fragrance Note, Very Natural Odor Impression.

16-Oxa-bicyclo[11.2.1]hexadecan-2-one E isomer $^1$H-NMR (CDCl$_3$, 400 MHz, TMS=0): 4.35 (J=8.2, J=6.8, 1H); 3.8 (J=4.65, 1H); 2.7 (J=5.4, J=12.7, J=10.9, 1H); 2.4 (J=5.4, J=12.7, J=10.9, 1H); 2.2 (1H); 2.05 (1H); 1.50-1.75 (4H) 1.20-1.50 (16H).

$^{13}$C-NMR (CDCl$_3$, 100 MHz): 215.8 (s), 83.0(d), 79.4 (d), 37.5 (t), 33.6 (t), 32.7 (t), 27.7 (t), 26.95 (t), 26.35 (t), 25.3 (t), 25.1 (t), 25.09 (t), 24.6 (t), 24.1 (t), 22.6 (t).

MS: m/z (%)=238 (13, M$^+$), 210 (23), 166 (7), 126 (10), 111 (16), 97 (47), 84 (74), 71 (89), 55 (100), 41(85), 29(34).

Odor Description, E-Isomer: Very Strong Clean Musk Odor, Interesting Delicate Erogenous Fragrance Note, Very Natural Odor Impression.

EXAMPLE 4

Odoriferous and/or Aroma Substance Composition (Perfume Composition)

| | |
|---|---|
| Agrumex LC | 10.00 |
| Amarocit ®, 10% in DPG | 10.00 |
| Ambroxide, crystalline | 10.00 |
| Basil oil | 10.00 |
| Calone 1951, 10% in DPG | 10.00 |
| Cedarwood oil | 10.00 |
| Cedrol, crystalline | 50.00 |
| Citral, 10% in DPG | 10.00 |
| Citronellol | 5.00 |
| Coumarin | 10.00 |
| Cyclogalbanat ®, 10% in DPG | 15.00 |
| Dihydromyrcenol | 80.00 |
| Farenal ®, 10% in DPG | 5.00 |
| Galbex, 10% in DPG | 25.00 |
| Globalide ® | 80.00 |
| Globanone ® | 40.00 |
| Hedione | 90.00 |
| Helional | 20.00 |
| Heliotropin | 5.00 |
| Hexenol, cis-3, 10% in DPG | 15.00 |
| Hexenyl salicylate, cis-3 | 10.00 |
| Beta-ionone | 5.00 |
| Iso E Super | 180.00 |
| Isodamascon ®, 10% in DPG | 10.00 |
| Isomuscone (cyclohexadecanone) | 20.00 |
| Isoraldein 70 | 20.00 |
| Ketamber, 10% in TEC | 25.00 |
| Lavandin grosso oil, nat. | 15.00 |
| Lilial | 20.00 |
| Linalool | 20.00 |
| Linalyl acetate | 40.00 |
| Mandarin oil, green, Brazilian | 50.00 |
| Timberol ® | 40.00 |
| Vanillin | 5.00 |
| Veloutone, 10% in DPG | 20.00 |
| Ysamber K ® | 10.00 |
| Total | 1000.00 |

DPG: dipropylene glycol,
TEC = triethyl citrate

Odor description of the perfume composition without addition of the compound of the formula (I): woody, flowery, tangy In the perfumers' opinion, the addition of 3 wt. % of the compound of the formula (I) from Example 1 renders this perfume composition fresher, more radiant, better rounded and more harmonious, a musk note appearing and the woody and flowery aspects being enhanced. The compound of formula I used impart distinctiveness to the composition due to their intrinsic odor and due to their modifying and enhancing action (booster action) and unite the different odorous elements.

EXAMPLE 5

Odoriferous and/or Aroma Substance Composition (Perfume Composition)

| | |
|---|---|
| Allylcyclohexyl propionate | 3.00 |
| Amyl salicylate | 2.00 |
| Benzyl acetate | 64.00 |
| Citronellol | 122.00 |
| Citral, 10% in DPG | 2.00 |
| Cyclamen aldehyde | 10.00 |
| Dihydromyrcenol | 3.00 |
| Dimethylbenzylcarbinyl acetate | 3.00 |
| Ethyl salicylate, 10% in DPG | 2.00 |
| Eugenol | 3.00 |
| Indoflor, 10% in DPG | 16.00 |
| Galaxolide, 50% in DPG | 164.00 |
| Geraniol | 35.00 |
| Dihydromethyl jasmonate | 6.00 |
| Heliotropin | 4.00 |
| Hexylcinnamaldehyde | 121.00 |
| Vertocitral | 4.00 |
| Hedione | 42.00 |
| Indole | 2.00 |
| Isobutyl salicylate | 6.00 |
| Lavandin grosso oil, nat. | 6.00 |

-continued

| | |
|---|---|
| Acetyl cedrene | 10.00 |
| Majantol | 190.00 |
| Linalool | 35.00 |
| Linalyl acetate | 10.00 |
| Methyl anthranilate, 10% in DPG | 5.00 |
| Nerol | 10.00 |
| Orange oil | 6.00 |
| Phantolide | 4.00 |
| Phenylacetaldehyde dimethylacetal | 6.00 |
| Phenylethyl alcohol | 75.00 |
| Florol | 6.00 |
| Sandalwood oil | 3.00 |
| Sandranol | 16.00 |
| Trifernal | 2.00 |
| Tonalid | 2.00 |
| Total | 1000.00 |

DPG: dipropylene glycol

Odor description for the perfume composition without addition of compounds of the formula (Ia): flowery, lily of the valley.

In the perfumers' opinion, due to the addition of 1 wt. % of the compound of the formula (Ia) from Example 3, this perfume composition gives a new lease of life. The impression of floweriness is considerably enhanced. The composition has more radiant, better rounded and more harmonious effect, a mellow, natural musk note appearing. The compound of the formula I used imparts distinctiveness to the composition due to their intrinsic odor and due to their modifying and enhancing action (booster action) and unites the different odorous elements.

EXAMPLE 6

Shampoo

The compounds of the formula (I) and/or formula (Ia) from Examples 1 and 3 were each incorporated separately at a rate of addition of 0.5 wt. % into a shampoo base of the following composition

| | |
|---|---|
| Sodium lauryl ether sulfate | 12% |
| (for example Texapon NSO from Cognis Germany GmbH) | |
| Cocamidopropyl betaine | 2% |
| (for example Dehyton K from Cognis Germany GmbH) | |
| Sodium chloride | 1.4% |
| Citric acid | 1.3% |
| Phenoxyethanol, methyl-, ethyl-, butyl-, and propylparaben | 0.5% |
| Water | 82.8% |

The pH value of the shampoo base was approx. 6. 100 ml of a 20 wt. % aqueous shampoo solution were produced therefrom, said solution comprising the compound either from Example 1 or Example 3. Two small strands of hair were washed together in these shampoo solutions for 2 minutes and then rinsed for 20 seconds under running, hand-warm water. For each shampoo solution, in each case one strand of hair was wrapped, while wet, in aluminum foil and the second strand was dried with a hairdryer. Both strands were assessed by a panel with regard to odor.

Odor description in each case: strong clean musk odor, interesting delicate erogenous fragrance note, very natural odor impression.

EXAMPLE 7

Rinse Conditioner

The perfume composition from Example 4 (after addition of 3 wt. % of the formula (I) compound from Example 1) was incorporated at a rate of addition of 0.5 wt. % into a rinse conditioner base of the following composition.

| | |
|---|---|
| Quarternary ammonium methosulfate (ester quat), approx. 90% (for example Rewoquat WE 18 from Witco Surfactants GmbH) | 5.5% |
| Alkyl dimethylbenzyl ammonium chloride, approx. 50% (for example Preventol R50 from Bayer AG) | 0.2% |
| Colorant solution, approx. 1% | 0.3% |
| Water | 94.0% |

The pH value of the rinse conditioner base was in the range from 2 to 3. Two pieces of fabric were rinsed in a Linetest machine in the rinse conditioning program for 30 minutes at 20° C. with 370 g of a 1% aqueous rinse conditioner solution based on the rinse conditioner base comprising 0.5 wt. % of the formula I compound. The pieces of fabric were wrung out and then spun for 20 seconds. One piece of fabric was heat-sealed while wet and one was hung up to dry. The two pieces of fabric were then assessed by a panel with regard to odor.

Odor description in each case: strong clean musk odor, interesting delicate erogenous fragrance note, very natural odor impression.

EXAMPLE 8

Washing Powder

The perfume oil composition from Example 4 (after addition of 6 wt. % of the formula (Ia) compound from Example 3) was incorporated at a rate of addition of 0.4 wt. % into a washing powder base of the following formulation.

| | |
|---|---|
| Linear sodium alkyl benzene sulfonate | 8.8% |
| Ethoxylated fatty alcohol C12-18 (7 EO) | 4.7% |
| Sodium soap | 3.2% |
| Defoamer DOW CORNING(R) 2-4248S POWDERED ANTIFOAM, Silicone oil on zeolite as carrier material | 3.9% |
| Zeolite 4A | 28.3% |
| Sodium carbonate | 11.6% |
| Sodium salt of a copolymer of acrylic and maleic acid (Sokalan CP5) | 2.4% |
| Sodium silicate | 3.0% |
| Carboxymethylcellulose | 1.2% |
| Dequest 2066 ([[(phosphonomethyl)imino]bis[(ethylenenitrilo)bis (methylene)]tetrakis-phosphonic acid, sodium salt) | 2.8% |
| Optical brightener | 0.2% |
| Sodium sulfate | 6.5% |
| Protease | 0.4% |
| Sodium perborate tetrahydrate | 22.0% |
| TAED | 1.0% |

Two pieces of fabric were washed in a Linetest machine in the main washing cycle for 45 minutes at 60° C. with 370 g of a 1% aqueous washing powder liquor based on the washing powder base comprising 0.4 wt. % of the perfume oil composition from Example 4 (the pH value of the washing powder liquor is distinctly in the basic range). The pieces of fabric were first rinsed for 5 minutes with cold water, wrung out and then spun for 20 seconds. One piece of fabric was heat-sealed while wet and one was hung up to dry. The two pieces of fabric were then assessed by a panel with regard to odor.

Odor description in each case: strong clean musk odor, interesting delicate erogenous fragrance note, very natural odor impression.

EXAMPLE 9

Odoriferous and/or Aroma Substance Composition (Perfume Composition)

| | |
|---|---|
| Allylcyclohexyl propionate | 3.00 |
| Amyl salicylate | 2.00 |
| Benzyl acetate | 64.00 |
| Citronellol | 122.00 |
| Citral, 10% in DPG | 2.00 |
| Cyclamen aldehyde | 10.00 |
| Dihydromyrcenol | 3.00 |
| Dimethylbenzylcarbinyl acetate | 3.00 |
| Ethyl salicylate, 10% in DPG | 2.00 |
| Eugenol | 3.00 |
| Indoflor, 10% in DPG | 16.00 |
| Galaxolide, 50% in DPG | 164.00 |
| Geraniol | 35.00 |
| Dihydromethyl jasmonate | 6.00 |
| Heliotropin | 4.00 |
| Hexylcinnamaldehyde | 121.00 |
| Vertocitral | 4.00 |
| Hedione | 42.00 |
| Indole | 2.00 |
| Isobutyl salicylate | 6.00 |
| Lavandin grosso oil, nat. | 6.00 |
| Acetyl cedrene | 10.00 |
| Majantol | 190.00 |
| Linalool | 35.00 |
| Linalyl acetate | 10.00 |
| Methyl anthranilate, 10% in DPG | 5.00 |
| Nerol | 10.00 |
| Orange oil | 6.00 |
| Phantolide | 4.00 |
| Phenylacetaldehyde dimethylacetal | 6.00 |
| Phenylethyl alcohol | 75.00 |
| Florol | 6.00 |
| Sandalwood oil | 3.00 |
| Sandranol | 16.00 |
| Trifernal | 2.00 |
| Tonalid | 2.00 |
| Total | 1000.00 |

DPG: dipropylene glycol

Odor description for the perfume composition without addition of compounds of the formula (I) and formula (Ia): flowery, lily of the valley.

In the perfumers' opinion, due to the addition of 2 wt. % of a 1:1 mixture of the compounds of the formula (I) and formula (Ia) from Examples 1 and 3, this perfume composition gives the impression of mellow, natural floweriness. The composition has more radiant, better rounded and more harmonious effect, a pleasant, erogenous musk note appearing. When used, the compounds of the formula I and formula (Ia) impart distinctiveness to the composition due to their intrinsic odor and due to their modifying and enhancing action (booster action) and unite the different odorous elements.

Further Embodiments

A first embodiment is compounds of the formula (I) and formula (Ia):

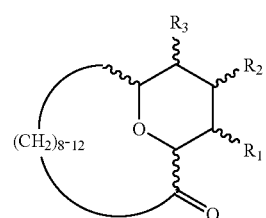

Formula (I)

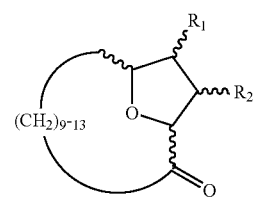

Formula (Ia)

wherein $R_1$, $R_2$ and $R_3$ mutually independently mean hydrogen or methyl.

A second embodiment is the compounds as described in the first embodiment, wherein for compounds of the formula (I)

$R_1$ means methyl and $R_2$ and $R_3$ mean hydrogen or $R_1$ and $R_3$ mean hydrogen and $R_2$ means methyl or $R_1$ and $R_2$ mean hydrogen and $R_3$ means methyl or $R_1$, $R_2$ and $R_3$ mean hydrogen.

A third embodiment is the compounds as described in the first or second embodiments selected from the group consisting of formula (I):

14-oxa-bicyclo[8.3.1]tetradecan-2-one, 15-oxa-bicyclo[9.3.1]pentadecan-2-one, 16-oxa-bicyclo[10.3.1]hexadecan-2-one, 17-oxa-bicyclo[11.3.1]-heptadecan-2-one, 18-oxa-bicyclo[12.3.1]octadecan-2-one, 13-methyl-16-Oxa-bicyclo[10.3.1]hexanedecan-2-on, 14-methyl-16-oxa-bicyclo[10.3.1]-hexadecan-2-one and 15-methyl-16-oxa-bicyclo[10.3.1]hexadecan-2-one.

A fourth embodiment is the compounds described in the first embodiment, wherein for compounds of the formula (I)

$R_1$ means methyl and $R_2$ means hydrogen or $R_1$ means hydrogen and $R_2$ means methyl or $R_1$ and $R_2$ mean methyl or $R_1$ and $R_2$ mean hydrogen, A fifth embodiment is the compounds as described in the first or fourth embodiment selected from the group consisting of formula (Ia):

15-oxa-bicyclo[9.2.1]tetradecan-2-one, 15-oxa-bicyclo[10.2.1]pentadecan-2-one, 16-oxa-bicyclo[11.2.1]hexadecan-2-one, 17-oxa-bicyclo[12.2.1 ]-heptadecan-2-one, 18-oxa-bicyclo[13.2.1]octadecan-2-one, 13-methyl-16-Oxa-bicyclo[9.3.1]hexanedecan-2-on, 14-methyl-16-oxa-bicyclo[11.2.1]-hexadecan-2-one and 15-methyl-16-oxa-bicyclo[11.2.1]hexadecan-2-one.

A sixth embodiment is an odoriferous and/or aroma substance composition comprising or consisting of a) one, two, three, four or more compounds of the formula (I) and/or formula (Ia) as described in any one of the first through fifth embodiments and
  b) one, two, three or more further odoriferous and/or aroma substances, which are not compounds of the formula (I) and formula (Ia).

A seventh embodiment is the composition described in the sixth embodiment, wherein the composition comprises a total quantity of the compounds of the formula (I) and/or formula (Ia) in component (a), which is sufficient in the composition to impart, modify and/or enhance an odor and/or flavor with one, a plurality of or all of the musk-like notes.

An eighth embodiment is the composition as described in the sixth or seventh embodiment, wherein the composition comprises a total quantity of one, two, three, four or more compounds of the formula (I) and/or formula (Ia) in component (a) which is sufficient
  to impart to this composition a radiance, roundness and/or harmony
  and/or
  to enhance the odor and/or flavor notes of the further odoriferous and/or aroma substance or one, two, three or more of the further odoriferous and/or aroma substances in component (b).

A ninth embodiment is the composition as described in any one of the sixth through eighth embodiments, wherein
  one, two, three or more odoriferous and/or aroma substances of the component (b) display a woody odor note and/or flavor note or
  one, two, three or more odoriferous and/or aroma substances of the component (b) display a flowery odor note and/or flavor note or
  one, two, three or more odoriferous and/or aroma substances of the component (b) display a woody and flowery odor note and/or flavor note.

A tenth embodiment is the composition as described in any one of the sixth through ninth embodiments, wherein the composition additionally comprises one or more solvents.

An eleventh embodiment is the composition as described in any one of the sixth through tenth embodiments, wherein the composition is partially or completely adsorbed on one or more carriers.

A twelfth embodiment is the composition as described in any one of the sixth through eleventh embodiments, wherein the composition is partially or completely microencapsulated and/or spray-dried or is present as inclusion complexes or as extrusion products.

A thirteenth embodiment is the composition as described in the twelfth embodiment, wherein the composition is coated with suitable materials for targeted odoriferous and/or aroma substance release A fourteenth embodiment is perfumed cosmetic or domestic products comprising or consisting of
  a) one, two, three, four or more compounds of the formula (I) and/or formula (Ia) as described in any one of the first through fifth embodiments and/or
  b) one, two, three or more odoriferous and/or aroma substance compositions as described in any one of the sixth through thirteenth embodiments
  and
  c) one or more further basic substances, auxiliary substances and/or additives.

A fifteenth embodiment is the products as described in the fourteenth embodiment, wherein the product is selected from the group consisting of:
  perfume extracts, eaux de parfum, eaux de toilette, shaving lotions, eaux de cologne, pre-shave products, splash colognes,
  perfumed tissue wipes,
  acidic, alkaline and neutral cleaning agents,
  disinfectants, surface disinfectants,
  air fresheners in liquid or gel form or applied to a solid carrier, aerosol sprays,
  waxes and polishes,
  bodycare products,
  hair care products,
  deodorants and antiperspirants,
  decorative cosmetic products,
  candles, lamp oils, incense sticks, insecticides, repellents, and propellants.

A sixteenth embodiment is aromatized products which serve for nutrition, oral care and/or pleasure, and semifinished products for this purpose or seasoning mixtures comprising or consisting of
  a) one, two, three, four or more compounds of the formula (I) and/or formula (Ia) as described in any one of the first through fifth embodiments and/or
  b) one, two, three or more odoriferous and/or aroma substance compositions as described in any one of the sixth through thirteenth embodiments
  and
  c) one or more further basic substances, auxiliary substances and/or additives.

A seventeenth embodiment is the products as described in the sixteenth embodiment, wherein the product which serves for nutrition, oral care and/or pleasure, a semifinished product or a seasoning mixtures is selected from the group consisting of:
  bakery products,
  confectionery,
  alcoholic or non-alcoholic beverages,
  instant beverages,
  meat products,
  eggs or egg products,
  cereal products,
  dairy products,
  products made from soy protein or other soybean fractions,
  fruit preparations,
  vegetable preparations,
  snacks,
  fat and oil based products or emulsions thereof,
  other ready meals and soups.

An eighteenth embodiment is the use of one, two, three, four or more compounds of the formula (I) and/or formula (Ia) as described in any one of the first through fifth embodiments as odoriferous and/or aroma substances.

A nineteenth embodiment is the use as described in the eighteenth embodiment as odoriferous and/or aroma substances with musk-like notes.

A twentieth embodiment is the use as described in the eighteenth or nineteenth embodiment, wherein one, two, three, four or more compounds of the formula (I) and/or formula (Ia) as described in any one of the first through fifth embodiments is/are used as an odoriferous and/or aroma substance in odoriferous and/or aroma compositions as described in any one of the sixth through thirteenth embodiments, a perfumed product as described in the fourteenth or fifteenth embodiment or an aromatized product as described in the sixteenth or seventeenth embodiment.

A twenty-first embodiment is the use as described in any one of the eighteenth through twentieth embodiments, wherein one, two, three, four or more compounds of the formula (I) and/or formula (Ia) is/are used to impart, modify and/or enhance an odor or flavor with one, a plurality of or all the musk-like notes.

A twenty-second embodiment is the use as described in any one of the eighteenth through twenty-first embodiments, wherein one or more compounds of the formula (I) and/or formula (Ia) is/are used as a booster.

A twenty-third embodiment is the use as described in any one of the eighteenth through twenty-second embodiments, wherein one, two, three, four or more compounds of the formula (I) and/or formula (Ia) is/are used to increase the substantivity of further odoriferous and/or aroma substances on skin, hair and/or textile fibers.

A twenty-fourth embodiment is the use as described in any one of the eighteenth through twenty-third embodiments, wherein one, two, three, four or more compounds of the formula (I) and/or formula (Ia) is/are used to increase the retention of further odoriferous and/or aroma substances.

A twenty-fifth embodiment is the use as described in any one of the eighteenth through twenty-fourth embodiments, wherein one, two, three, four or more compounds of the formula (I) and/or formula (Ia) is/are used to impart radiance, roundness and/or harmony and/or to enhance odor and/or flavor notes in odoriferous and/or aroma substance compositions.

A twenty-sixth embodiment is a method of imparting, modifying and/or enhancing an odor or flavor with one, a plurality of or all of the musk-like notes, wherein an organoleptically effective quantity of one, two, three, four or more compounds of the formula (I) and/or formula (Ia) as described in any one of the first through fifth embodiments or an organoleptically effective quantity of one or more odoriferous and/or aroma substance compositions as described in any one of the sixth through thirteenth embodiments comprising one, two, three, four or more compounds of the formula (I) and/or formula (Ia) as described in any one of the first through fifth embodiments is/are brought into contact or mixed with a product.

A twenty-seventh embodiment is the method of producing one or more compounds of the formula (I) as described in any one of the first through third embodiments
comprising or consisting of the following steps:
a) epoxidation of a compound of the formula (II) to yield a corresponding compound of the formula (III)

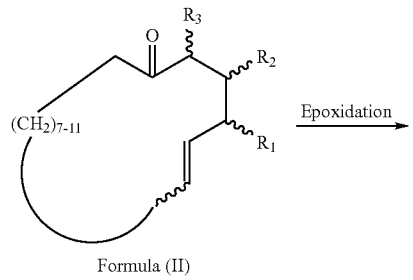

Formula (II)

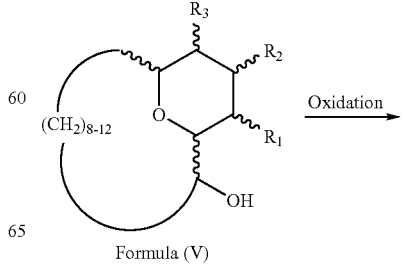

Formula (III)

wherein $R_1$, $R_2$ and $R_3$ have the above-stated meanings, b) subsequent reduction of the corresponding compound of the formula (III) to yield a corresponding compound of the formula (IV)

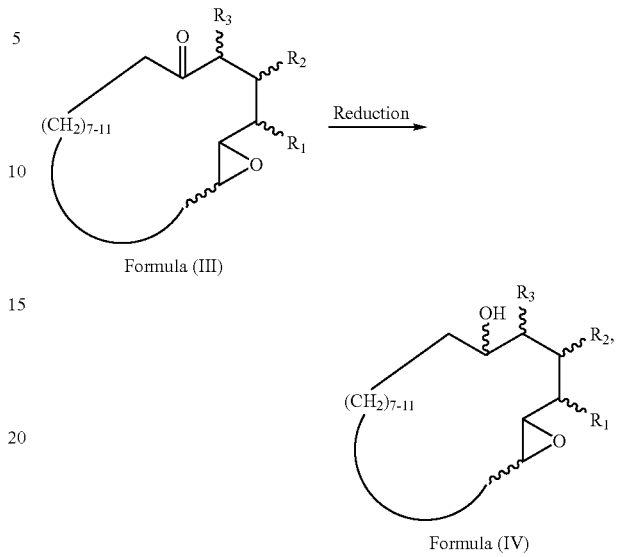

wherein $R_1$, $R_2$ and $R_3$ have the above-stated meanings, c) subsequent cyclization of the corresponding compound of the formula (IV) to yield a corresponding compound of the formula (V)

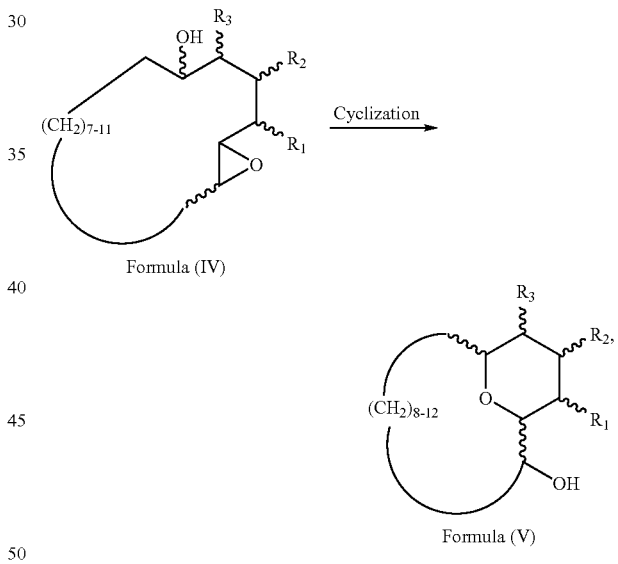

wherein $R_1$, $R_2$ and $R_3$ have the above-stated meanings and d) subsequent oxidation of the corresponding compound of the formula (V) to yield a corresponding compound of the formula (I)

-continued

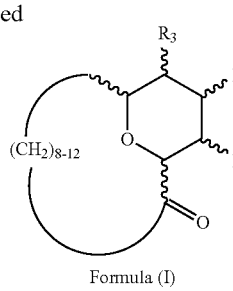

Formula (I)

wherein $R_1$, $R_2$ and $R_3$ have the above-stated meanings.

A twenty-eighth embodiment is the method of producing one or more compounds of the formula (Ia) as described in any one of the first fourth, or fifth embodiments comprising or consisting of the following steps:

a) reduction of a compound of the formula (IIa) to yield a corresponding compound of the formula (IIIa)

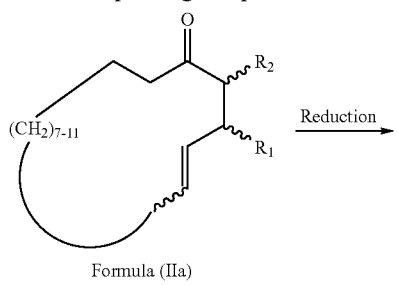

Formula (IIa)

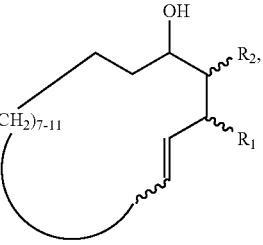

Formula (IIIa)

wherein $R_1$ and $R_2$ have the above-stated meanings b) subsequent epoxidation of the corresponding compound of the formula (IIIa) to yield a corresponding compound of the formula (IVa)

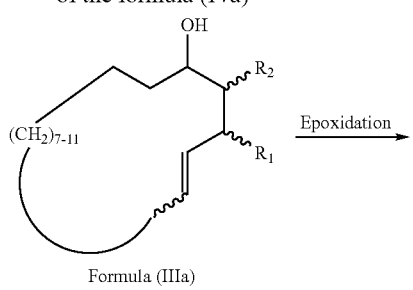

Formula (IIIa)

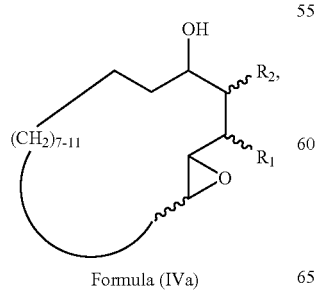

Formula (IVa)

wherein $R_1$ and $R_2$ have the above-stated meanings, c) subsequent cyclization of the corresponding compound of the formula (IVa) to yield a corresponding compound of the formula (Va)

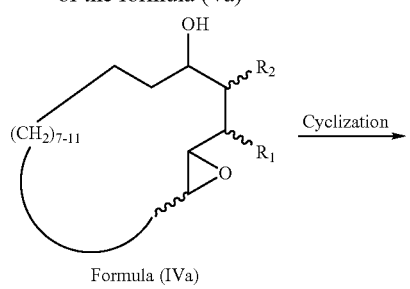

Formula (IVa)

Formula (Va)

wherein $R_1$ and $R_2$ have the above-stated meanings and d) subsequent oxidation of the corresponding compound of the formula (Va) to yield a corresponding compound of the formula (Ia)

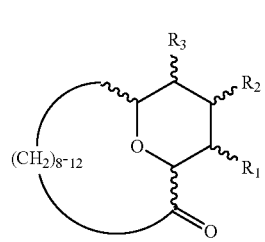

Formula (Va)

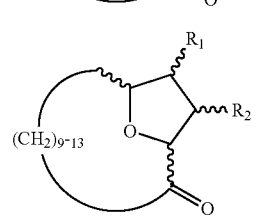

Formula (Ia)

wherein $R_1$ and $R_2$ have the above-stated meanings.

The invention claimed is:

1. Compounds of the formula (I) and/or formula (Ia):

Formula (I)

Formula (Ia)

wherein $R_1$, $R_2$ and $R_3$ are independently hydrogen or methyl.

2. The compounds of claim 1, wherein for compounds of the formula (I)
$R_1$ is methyl and $R_2$ and $R_3$ are hydrogen; or
$R_1$ and $R_3$ are hydrogen and $R_2$ is methyl; or
$R_1$ and $R_2$ are hydrogen and $R_3$ is methyl; or
$R_1$, $R_2$ and $R_3$ are hydrogen.

3. The compounds of claim 1, wherein the compound of the formula (I) is selected from the group consisting of:
14-oxa-bicyclo[8.3.1]tetradecan-2-one, 15-oxa-bicyclo[9.3.1]pentadecan-2-one, 16-oxa-bicyclo[10.3.1]hexadecan-2-one, 17-oxa-bicyclo[11.3.1]heptadecan-2-one, 18-oxa-bicyclo[12.3.1]octadecan-2-one, 13-methyl-16-Oxa-bicyclo[10.3.1]hexanedecan-2-on, 14-methyl-16-oxa-bicyclo[10.3.1]hexadecan-2-one and 15-methyl-16-oxa-bicyclo[10.3.1]hexadecan-2-one.

4. The compounds of claim 1, wherein for compounds of the formula (I)
$R_1$ is methyl and $R_2$ is hydrogen; or
$R_1$ is hydrogen and $R_2$ is methyl; or
$R_1$ and $R_2$ are methyl; or
$R_1$ and $R_2$ are hydrogen.

5. The compounds of claim 1, wherein the compound of formula (Ia) is selected from the group consisting of:
15-oxa-bicyclo[9.2.1]tetradecan-2-one, 15-oxa-bicyclo[10.2.1]pentadecan-2-one, 16-oxa-bicyclo[11.2.1]hexadecan-2-one, 17-oxa-bicyclo[12.2.1]heptadecan-2-one, 18-oxa-bicyclo[13.2.1]octadecan-2-one, 13-methyl-16-Oxa-bicyclo[9.3.1]hexanedecan-2-on, 14-methyl-16-oxa-bicyclo[11.2.1]hexadecan-2-one and 15-methyl-16-oxa-bicyclo[11.2.1]hexadecan-2-one.

6. An odoriferous and/or aroma substance composition comprising
a) one or more compounds of the formula (I) and/or formula (Ia)

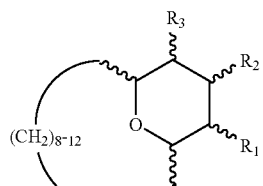

Formula (I)

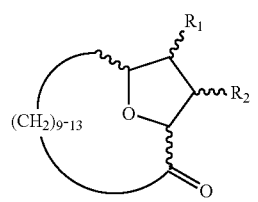

Formula (Ia)

wherein $R_1$, $R_2$ and $R_3$ are independently hydrogen or methyl; and
b) one or more further odoriferous and/or aroma substances, which are not compounds of the formula (I) and formula (Ia).

7. The composition of claim 6, wherein the composition comprises a total quantity of the compounds of the formula (I) and/or formula (Ia) which is sufficient in the composition to impart, modify and/or enhance an odor and/or flavor with one or more musk-like notes.

8. The composition of claim 6, wherein the composition comprises a total quantity of one or more compounds of the formula (I) and/or formula (Ia) in component (a) which is sufficient to impart to this composition a radiance, roundness and/or harmony
and/or
to enhance the odor and/or flavor notes of the one or more further odoriferous and/or aroma substances.

9. The composition of claim 6, wherein
the one or more further odoriferous and/or aroma substances of component (b) display a woody odor note and/or flavor note; or
the one or more further odoriferous and/or aroma substances of component (b) display a flowery odor note and/or flavor note; or
the one or more further odoriferous and/or aroma substances of component (b) display a woody and flowery odor note and/or flavor note.

10. The composition of claim 6, further comprising one or more solvents.

11. The composition of claim 6, wherein the composition is partially or completely adsorbed on one or more carriers.

12. The composition of claim 6, wherein the composition is partially or completely microencapsulated and/or spray-dried or is present as inclusion complexes or as extrusion products.

13. The composition of claim 12, wherein the composition is coated with suitable materials for targeted odoriferous and/or aroma substance release.

14. A perfumed cosmetic or domestic product comprising
a) one or more compounds of the formula (I) and/or formula (Ia)

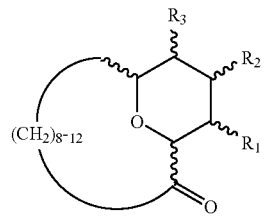

Formula (I)

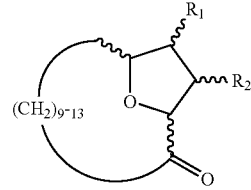

Formula (Ia)

wherein $R_1$, $R_2$ and $R_3$ are independently hydrogen or methyl;
b) one or more odoriferous and/or aroma substance compositions comprising:
a. one or more compounds of the formula (I) and/or formula (Ia); and
b. one or more further odoriferous and/or aroma substances, which are not compounds of the formula (I) and formula (Ia); and
c) one or more further basic substances, auxiliary substances and/or additives.

15. The product of claim 14, wherein the product is selected from the group consisting of
perfume extracts, eaux de parfum, eaux de toilette, shaving lotions, eaux de cologne, pre-shave products, splash colognes,
perfumed tissue wipes,
acidic, alkaline and neutral cleaning agents,
disinfectants, surface disinfectants, air fresheners in liquid or gel form or applied to a solid carrier, aerosol sprays,
waxes and polishes,
bodycare products,
hair care products,
deodorants and antiperspirants,
decorative cosmetic products,
candles, lamp oils, incense sticks, insecticides, repellents, and propellants.

16. A compound comprising an aromatized product which serves for nutrition, oral care and/or pleasure, and semifinished products for this purpose or seasoning mixtures, said product comprising:
a) one or more compounds of the formula (I) and/or formula (Ia)

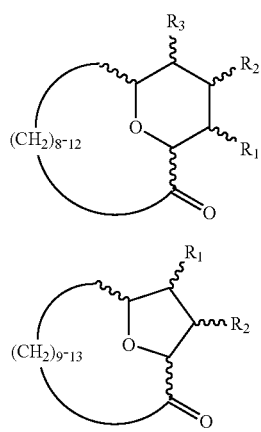

Formula (I)

Formula (Ia)

wherein $R_1$, $R_2$ and $R_3$ are independently hydrogen or methyl;
b) one or more odoriferous and/or aroma substance compositions comprising
   a. one or more compounds of the formula (I) and/or formula (Ia); and
   b. one or more further odoriferous and/or aroma substances, which are not compounds of the formula (I) and formula (Ia); and
c) one or more further basic substances, auxiliary substances and/or additives.

17. The compound of claim 16, wherein the product is selected from the group consisting of:
bakery products,
confectionery,
alcoholic or non-alcoholic beverages,
instant beverages,
meat products,
eggs or egg products,
cereal products,
dairy products,
products made from soy protein or other soybean fractions,
fruit preparations,
vegetable preparations,
snacks,
fat and oil based products or emulsions thereof,
other ready meals and soups.

18. A method of imparting, modifying and/or enhancing an odor or flavor with one or more musk-like notes, comprising:
contacting a product with either an organoleptically effective quantity of one or more compounds of the formula (I) and/or formula (Ia)

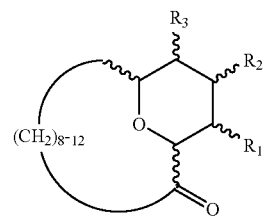

Formula (I)

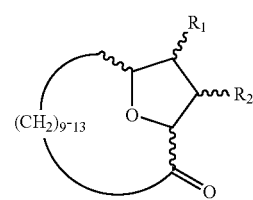

Formula (Ia)

wherein $R_1$, $R_2$ and $R_3$ are independently hydrogen or methyl;
or an organoleptically effective quantity of one or more odoriferous and/or aroma substances comprising
   a. one or more compounds of the formula (I) and/or formula (Ia); and
   b. one or more further odoriferous and/or aroma substances, which are not compounds of the formula (I) and formula (Ia).

19. A method of producing one or more compounds of the formula (I)

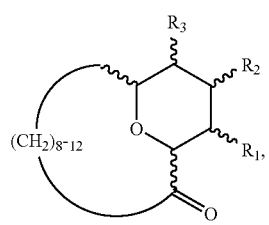

Formula (I)

wherein $R_1$, $R_2$ and $R_3$ are independently hydrogen or methyl, comprising:
a) epoxidating a compound of the formula (II) to yield a corresponding compound of the formula (III)

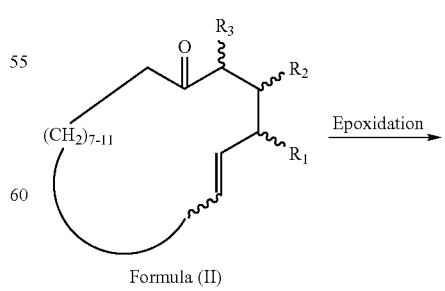

Formula (II)

-continued

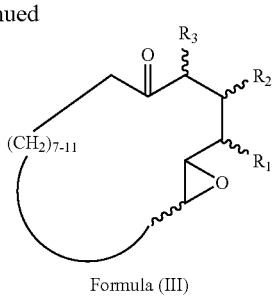

Formula (III)

wherein $R_1$, $R_2$ and $R_3$ have the above-stated meanings,
b) subsequently reducing the corresponding compound of the formula (III) to yield a corresponding compound of the formula (IV)

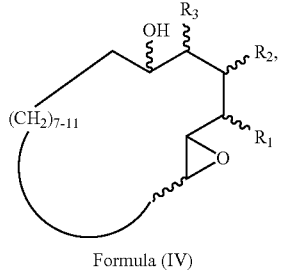

Formula (III)

→ Reduction

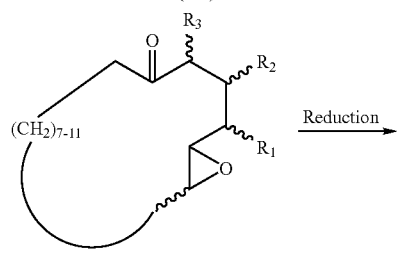

Formula (IV)

wherein $R_1$, $R_2$ and $R_3$ have the above-stated meanings,
c) subsequently cyclizing the corresponding compound of the formula (IV) to yield a corresponding compound of the formula (V)

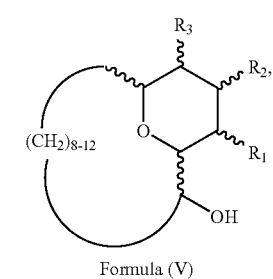

Formula (IV)

→ Cyclization

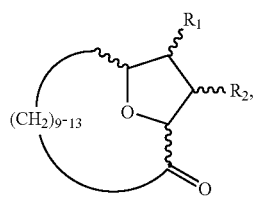

Formula (V)

wherein $R_1$, $R_2$ and $R_3$ have the above-stated meanings; and d) subsequently oxidizing the corresponding compound of the formula (V) to yield a corresponding compound of the formula (I)

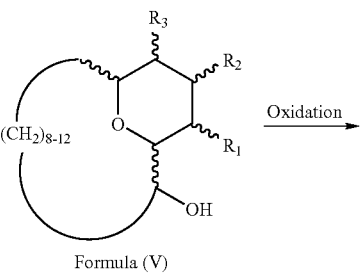

Formula (V)

→ Oxidation

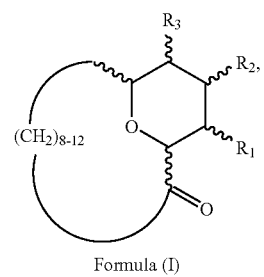

Formula (I)

wherein $R_1$, $R_2$ and $R_3$ have the above-stated meanings.

20. A method for producing one or more compounds of the formula (Ia)

Formula (Ia)

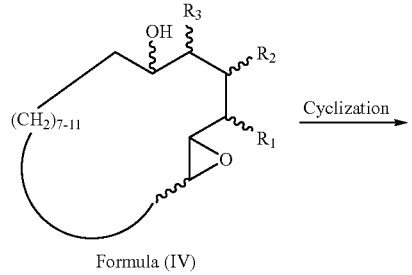

wherein $R_1$ and $R_2$ are independently hydrogen or methyl, comprising:
a) reducing a compound of the formula (IIa) to yield a corresponding compound of the formula (IIIa)

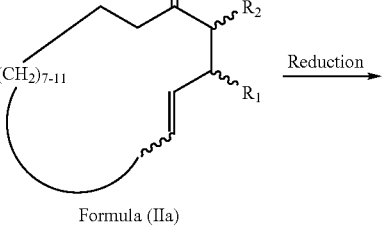

Formula (IIa)

→ Reduction

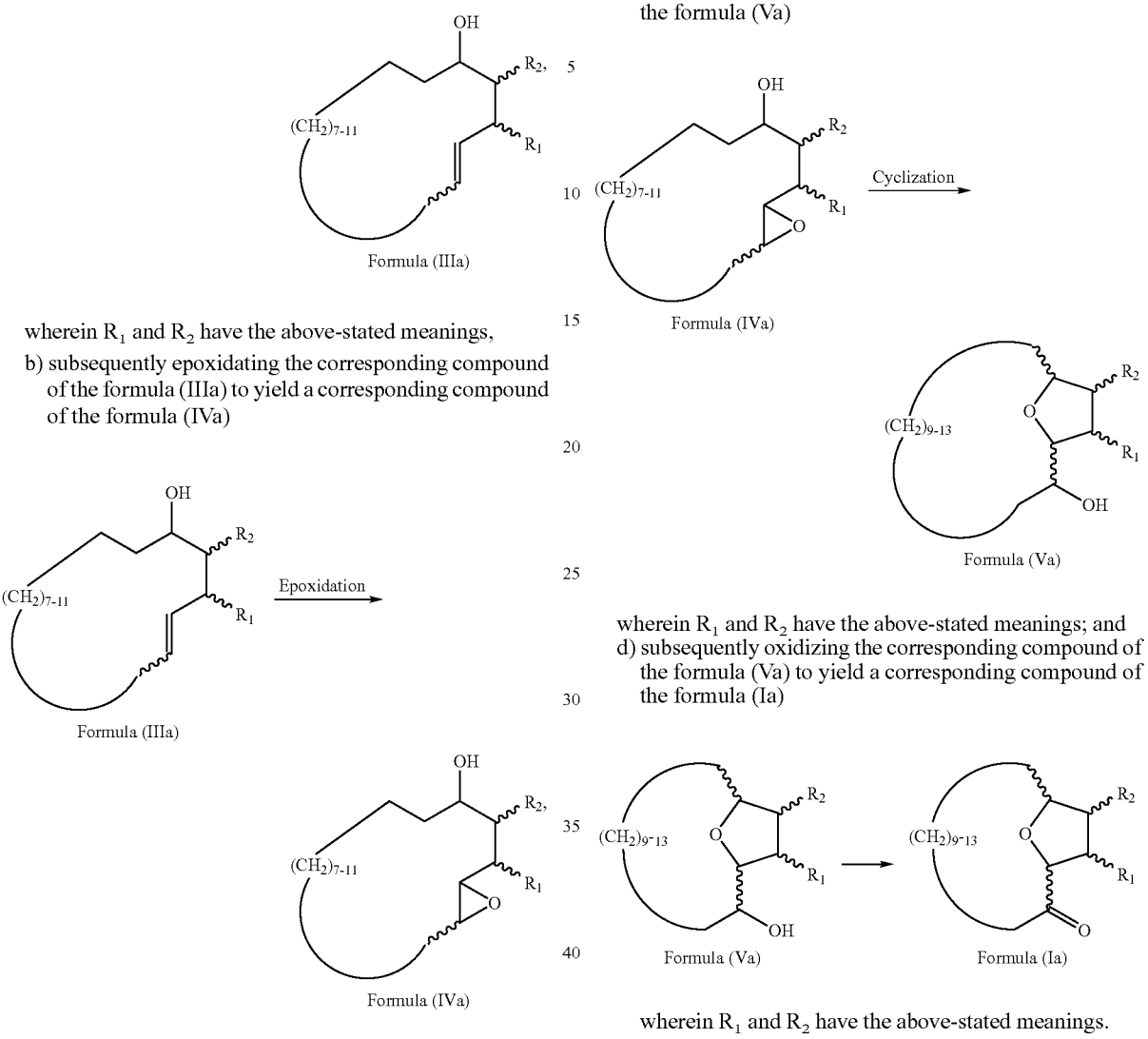

wherein $R_1$ and $R_2$ have the above-stated meanings, b) subsequently epoxidating the corresponding compound of the formula (IIIa) to yield a corresponding compound of the formula (IVa)

wherein $R_1$ and $R_2$ have the above-stated meanings, c) subsequently cyclizing the corresponding compound of the formula (IVa) to yield a corresponding compound of the formula (Va)

wherein $R_1$ and $R_2$ have the above-stated meanings; and d) subsequently oxidizing the corresponding compound of the formula (Va) to yield a corresponding compound of the formula (Ia)

wherein $R_1$ and $R_2$ have the above-stated meanings.

* * * * *